US012121627B2

(12) United States Patent
Manuel et al.

(10) Patent No.: US 12,121,627 B2
(45) Date of Patent: *Oct. 22, 2024

(54) BIORESORBABLE METAL ALLOY AND IMPLANTS

(71) Applicant: University of Florida Research Foundation, Inc., Gainesville, FL (US)

(72) Inventors: Michele Viola Manuel, Gainesville, FL (US); Ida E. Svensson Berglund, Chicago, IL (US); Benjamin G. Keselowsky, Gainesville, FL (US); Malisa Sarntinoranont, Gainesville, FL (US); Harpreet Singh Brar, Hillsboro, OR (US); Hunter B. Henderson, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 149 days.

This patent is subject to a terminal disclaimer.

(21) Appl. No.: 17/953,407

(22) Filed: Sep. 27, 2022

(65) Prior Publication Data

US 2023/0037160 A1 Feb. 2, 2023

Related U.S. Application Data

(63) Continuation of application No. 15/381,163, filed on Dec. 16, 2016, now Pat. No. 11,491,257, which is a continuation-in-part of application No. 13/808,037, filed as application No. PCT/US2011/042892 on Jul. 2, 2011, now Pat. No. 9,629,873.

(60) Provisional application No. 61/361,327, filed on Jul. 2, 2010.

(51) Int. Cl.
*A61L 27/04* (2006.01)
*A61K 33/06* (2006.01)
*A61L 27/54* (2006.01)
*A61L 27/58* (2006.01)
*A61L 31/02* (2006.01)
*A61L 31/14* (2006.01)
*A61L 31/16* (2006.01)
*C22C 23/00* (2006.01)

(52) U.S. Cl.
CPC ............ *A61L 27/047* (2013.01); *A61K 33/06* (2013.01); *A61L 27/54* (2013.01); *A61L 27/58* (2013.01); *A61L 31/022* (2013.01); *A61L 31/148* (2013.01); *A61L 31/16* (2013.01); *C22C 23/00* (2013.01); *A61L 2300/258* (2013.01); *A61L 2300/414* (2013.01); *A61L 2300/43* (2013.01); *A61L 2430/02* (2013.01); *A61L 2430/12* (2013.01); *A61L 2430/38* (2013.01)

(58) Field of Classification Search
CPC ........ A61L 27/047; A61L 27/54; A61L 27/58; A61L 2430/12; A61L 2430/38; C22C 23/00; A61K 33/06
See application file for complete search history.

(56) References Cited

U.S. PATENT DOCUMENTS

| | | | |
|---|---|---|---|
| 2,073,515 A * | 3/1937 | Fischer | C22C 23/00 |
| | | | 420/402 |
| 2,380,200 A | 7/1945 | Stroup et al. | |
| 5,015,863 A | 5/1991 | Takeshima et al. | |
| 5,925,313 A | 7/1999 | Kajihara et al. | |
| 6,896,517 B1 | 5/2005 | Goeran | |
| 7,771,774 B2 | 8/2010 | Berckmans, III | |
| 9,629,873 B2 * | 4/2017 | Manuel | A61K 33/06 |
| 11,491,257 B2 * | 11/2022 | Manuel | A61L 27/047 |
| 2003/0087197 A1 | 5/2003 | Schulman | |
| 2004/0241314 A1 | 12/2004 | Li | |
| 2005/0079200 A1 * | 4/2005 | Rathenow | A61L 31/10 |
| | | | 427/2.24 |
| 2005/0250073 A1 | 11/2005 | Tresser | |
| 2005/0266041 A1 | 12/2005 | Gerold et al. | |
| 2006/0198869 A1 | 9/2006 | Furst et al. | |
| 2007/0169859 A1 | 7/2007 | Kawamura et al. | |
| 2008/0075624 A1 | 3/2008 | Sakai et al. | |
| 2008/0152532 A1 | 6/2008 | Nakata et al. | |
| 2008/0243242 A1 | 10/2008 | Gerhard | |
| 2008/0312736 A1 | 12/2008 | Mueller | |
| 2009/0081313 A1 | 3/2009 | Aghion et al. | |
| 2009/0131540 A1 | 5/2009 | Hiromoto | |
| 2009/0171452 A1 | 7/2009 | Yamamoto et al. | |
| 2009/0175754 A1 | 7/2009 | Wilks et al. | |
| 2009/0226857 A1 | 9/2009 | Grant | |
| 2010/0075162 A1 * | 3/2010 | Yang | A61L 27/306 |
| | | | 427/2.24 |
| 2010/0161031 A1 | 6/2010 | Papirov et al. | |
| 2010/0262239 A1 * | 10/2010 | Boyden | A61F 2/30 |
| | | | 600/587 |

(Continued)

FOREIGN PATENT DOCUMENTS

CN 102260812 11/2011
DE 19905702 5/2000

(Continued)

OTHER PUBLICATIONS

Anyanwu, et al., "Creep Properties of Mg—Gd—Y—Zr Alloys", Materials Transactions, vol. 42, No. 7, 2001, 1212-1218.

(Continued)

*Primary Examiner* — Michael B. Pallay
(74) *Attorney, Agent, or Firm* — Thomas | Horstemeyer, LLP

(57) ABSTRACT

Embodiments of the present disclosure provide for structures including an alloy of calcium, strontium, and magnesium.

12 Claims, 25 Drawing Sheets

(56) References Cited

U.S. PATENT DOCUMENTS

| | | |
|---|---|---|
| 2010/0310409 A1 | 12/2010 | Gibson et al. |
| 2011/0054629 A1 | 3/2011 | Seok et al. |
| 2011/0070120 A1 | 3/2011 | Kim et al. |
| 2011/0076319 A1 | 3/2011 | Orlowski et al. |
| 2011/0319986 A1 | 12/2011 | Bayer |
| 2012/0148871 A1 | 6/2012 | Stoermer et al. |
| 2013/0144290 A1 | 6/2013 | Schiffl et al. |
| 2013/0199677 A1 | 8/2013 | Venkatesan et al. |
| 2014/0248288 A1 | 9/2014 | Kumta et al. |
| 2014/0373982 A1 | 12/2014 | Chen et al. |

FOREIGN PATENT DOCUMENTS

| | | |
|---|---|---|
| EP | 0261470 | 3/1988 |
| EP | 0263274 | 4/1988 |
| EP | 2014319 | 1/2009 |
| EP | 2022443 | 2/2009 |
| EP | 2119414 | 11/2009 |
| EP | 2355108 | 8/2011 |
| KR | 10-2008-0027202 | 3/2008 |
| KR | 10-2009-0099670 | 9/2009 |
| WO | 1990006581 | 6/1990 |
| WO | 1998000258 | 1/1998 |
| WO | WO2006096720 | 9/2006 |
| WO | WO20111 05685 | 9/2011 |

OTHER PUBLICATIONS

He, et al., "Comparison of the microstructure and mechanical properties of a ZK60 alloy with and without 1.3 wt. % gadolinium addition", Materials Science and Engineering, A, 433, 2006, 175-181.

International Search Report and Written Opinion for Application No. PCT/US2016/013784 Filing Date Jan. 18, 2016; Mailing Date Jun. 10, 2016 (11 Pages).

Brar, H. S. et al. "A study of biodegradable Mg—3So—3Y alloy and the effect of surface passivation on in-vitro degradation" Acta Biomaterialia 9 (2013) 5331-5340.

Chen SL, DanielS, Zhang F, Chang YA, Yan XY, Xie FY, Schmid-Fetzer R, Oates WA. "The PANDAT Software Package and its Applications" CALPHAD 2002; 26: (175-188).

International Preliminary Report on Patentability for Application No. PCT/US2011/042892 Filing Date Jul. 2, 2011; Issue Date Jan. 8, 2013 (6 pages).

International Search Report for Application No. PCT/US2011/042892 Filing Date Jul. 2, 2011; Mailing Date Mar. 20, 2012 (4 pages).

Li Z, Gu X, Lou S, Zheng Y. "The development of binary Mg—Ca alloys for use as biodegradable materials within bone" Biomaterials 2007; 29: (1329-1344).

Written Opinion for Application No. PCT/US2011/042892 Filing Date Jul. 2, 2011; Mailing Date Mar. 20, 2012 (5 pages).

Ida S. Berglund, et al.; Synthesis and Characterization of Mg—Ca—Sr Alloys for Biodegradable Orthopedic Implant Applications; Society for Biomaterials; Jun. 12, 2012; pp. 1524-1534.

M. Bornapour, et al.; Biocompatibility and Biodegradability of Mg—Sr Alloys: The Formation of Sr-Substituted Hydroxyapatite; Acta Biomaterialia vol. 9 (2013); Aug. 5, 2012; pp. 5319-5330.

Brar, et al. "Investigation of the mechanical and degradation properties of Mg—Sr and Mg—Zn—Sr alloys for use as potential biodegradable implant materials." Journal of the Mechanical Behavior of Biomedical Materials 7 (2012) 87-95.

International Search Report for Application No. PCT/US2014/064065 Filing Date Nov. 5, 2014; Mailing Date Feb. 18, 2015 (8 pages).

Written Opinion for Application No. PCT/US2014/064065 Filing Date Nov. 5, 2014; Mailing Date Feb. 18, 2015 (5 pages).

International Search Report for Application No. PCT/US2014/045364 Filing Date Jul. 3, 2014; Mailing Date Oct. 28, 2014 (6 pages).

Written Opinion for International Application No. PCT/US2014/045364 Filing Date Jul. 3, 2014; Mailing Date Oct. 28, 2014 (9 pages).

\* cited by examiner

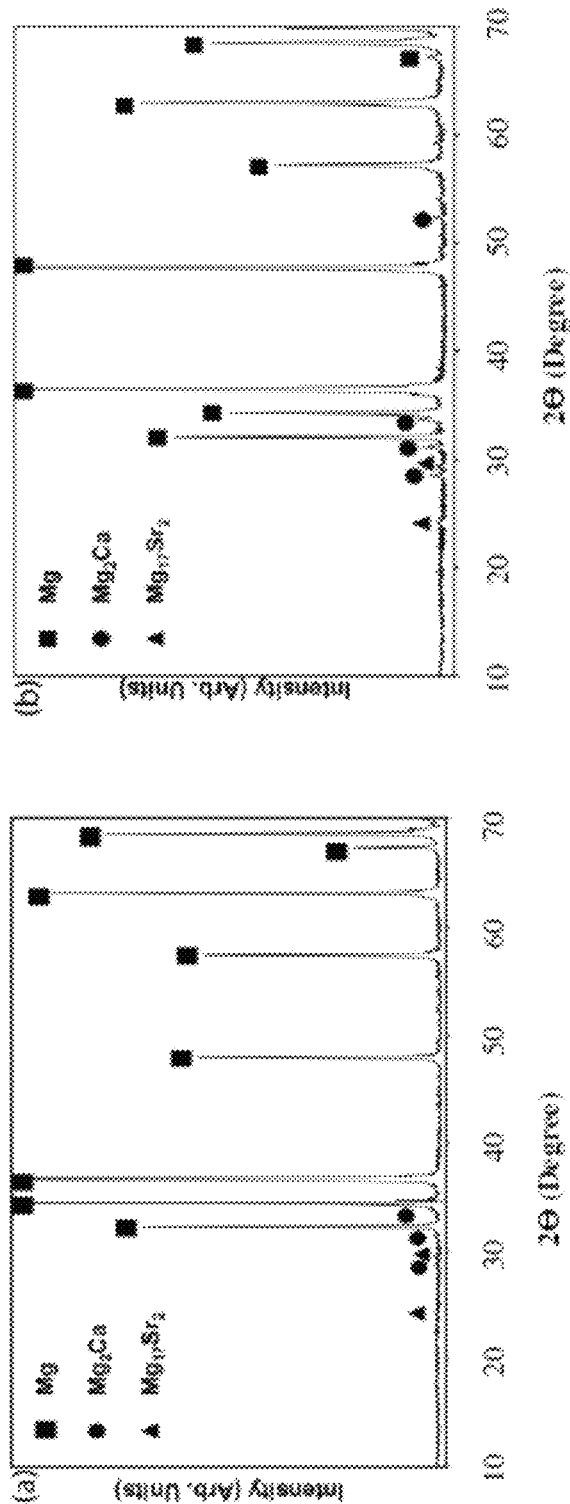
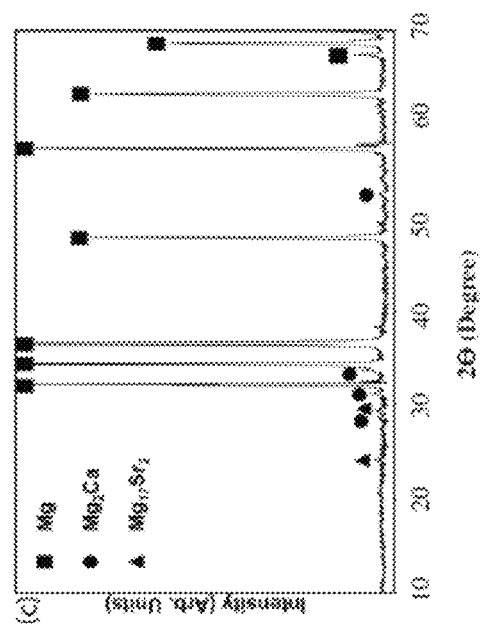
Fig. 3A
Fig. 3B
Fig. 3C

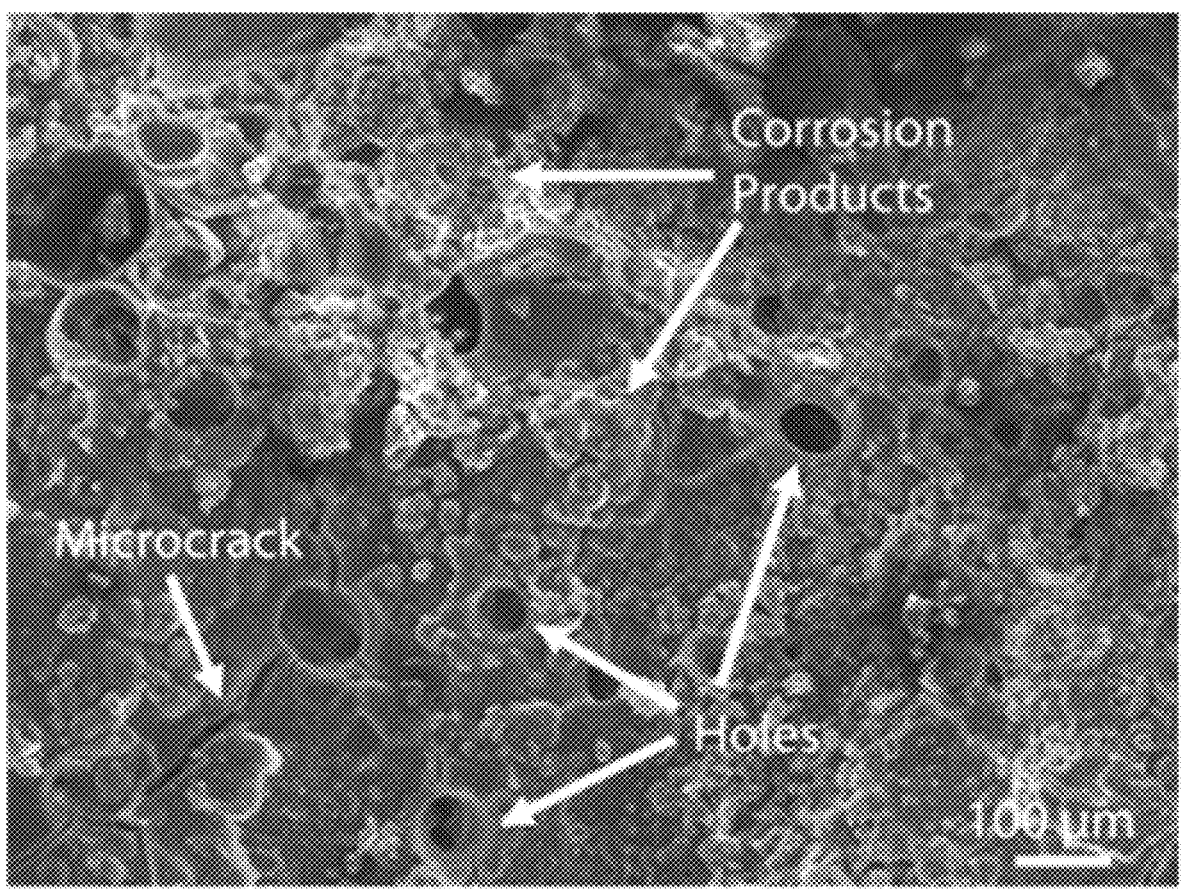
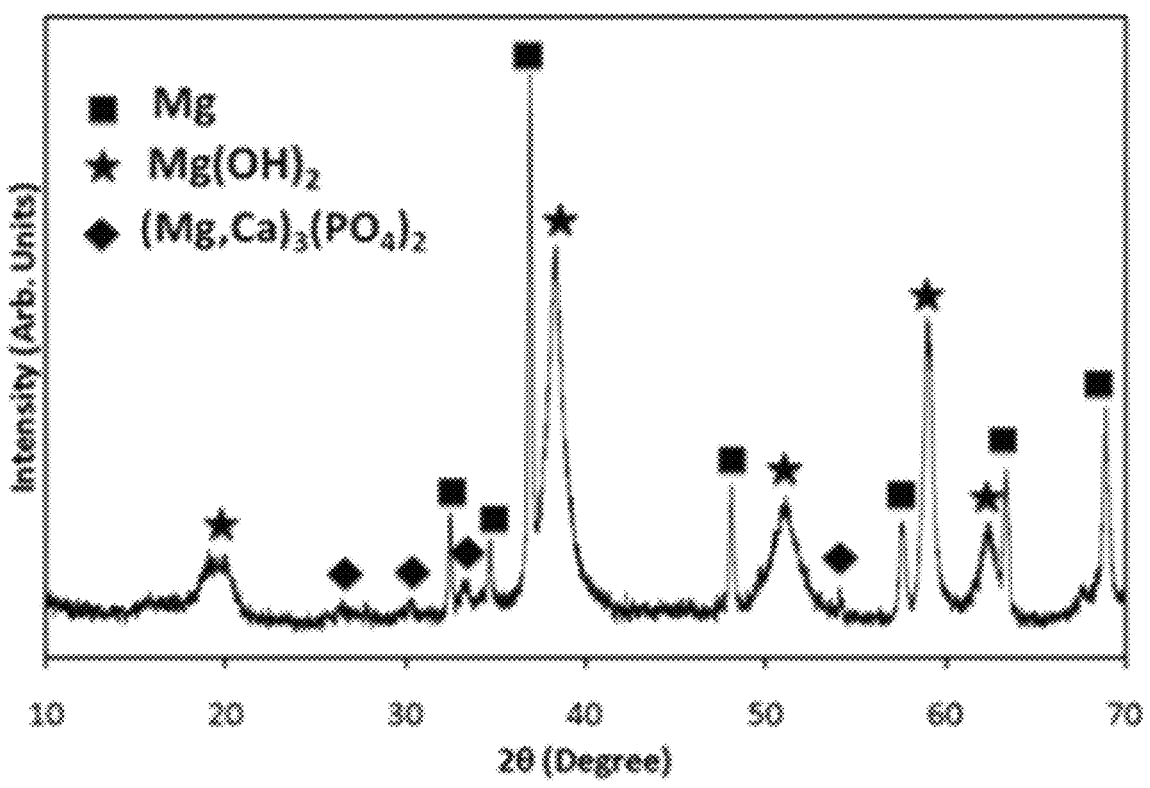
Fig. 6

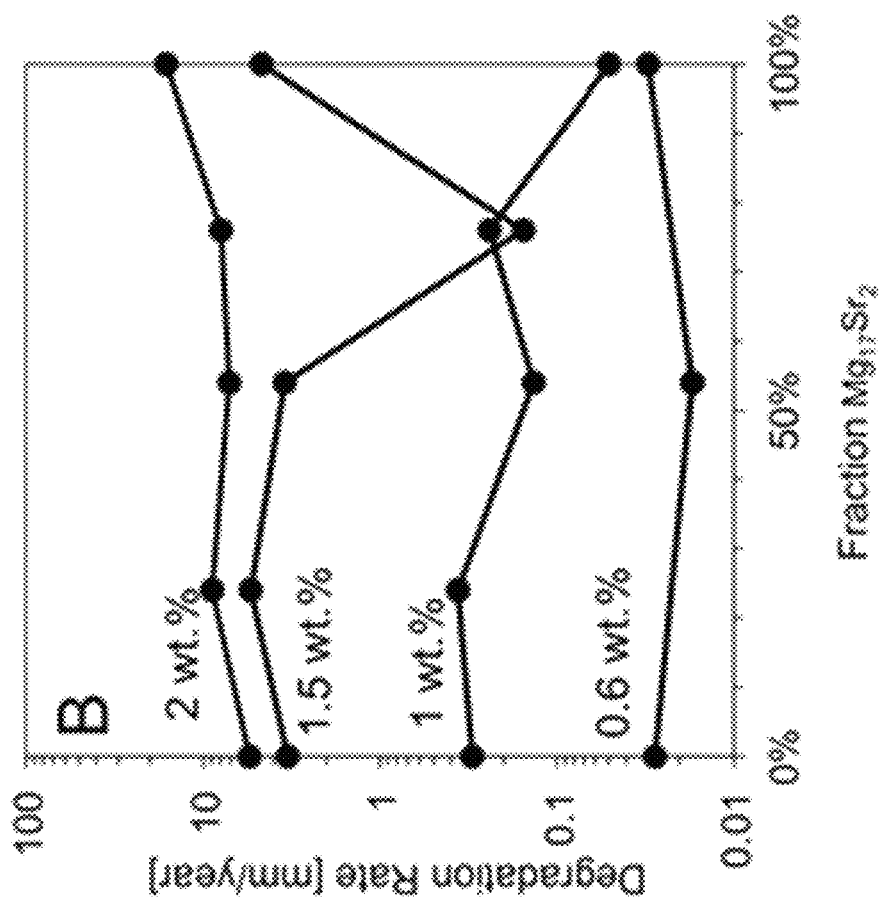
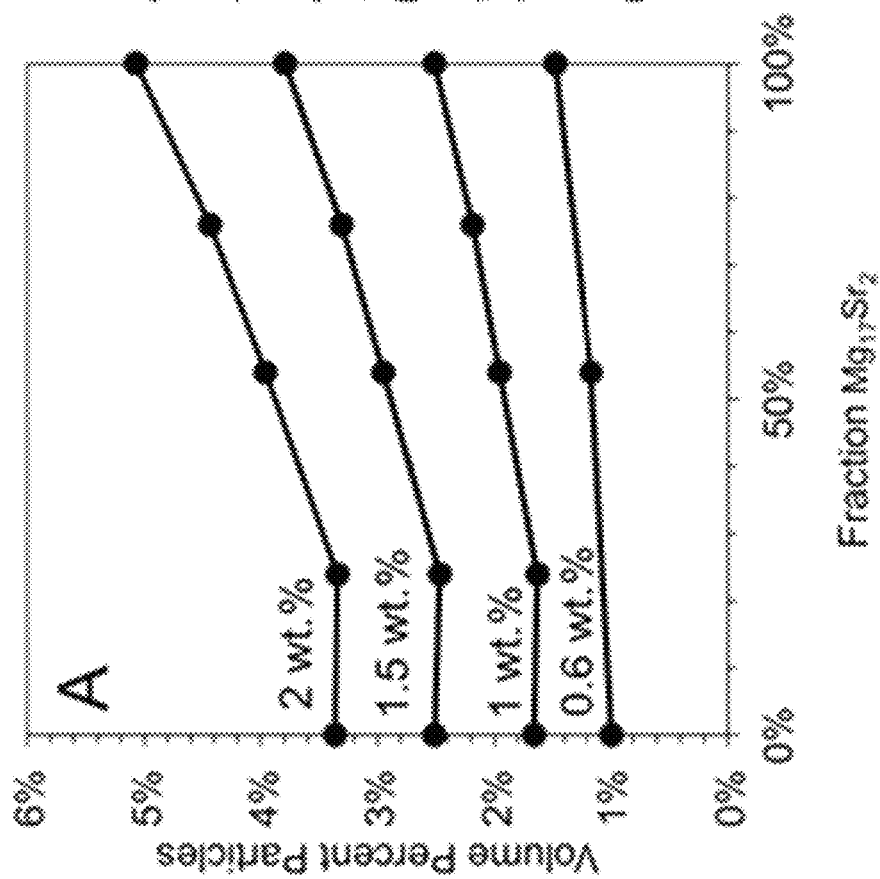
Fig. 16B
Fig. 16A

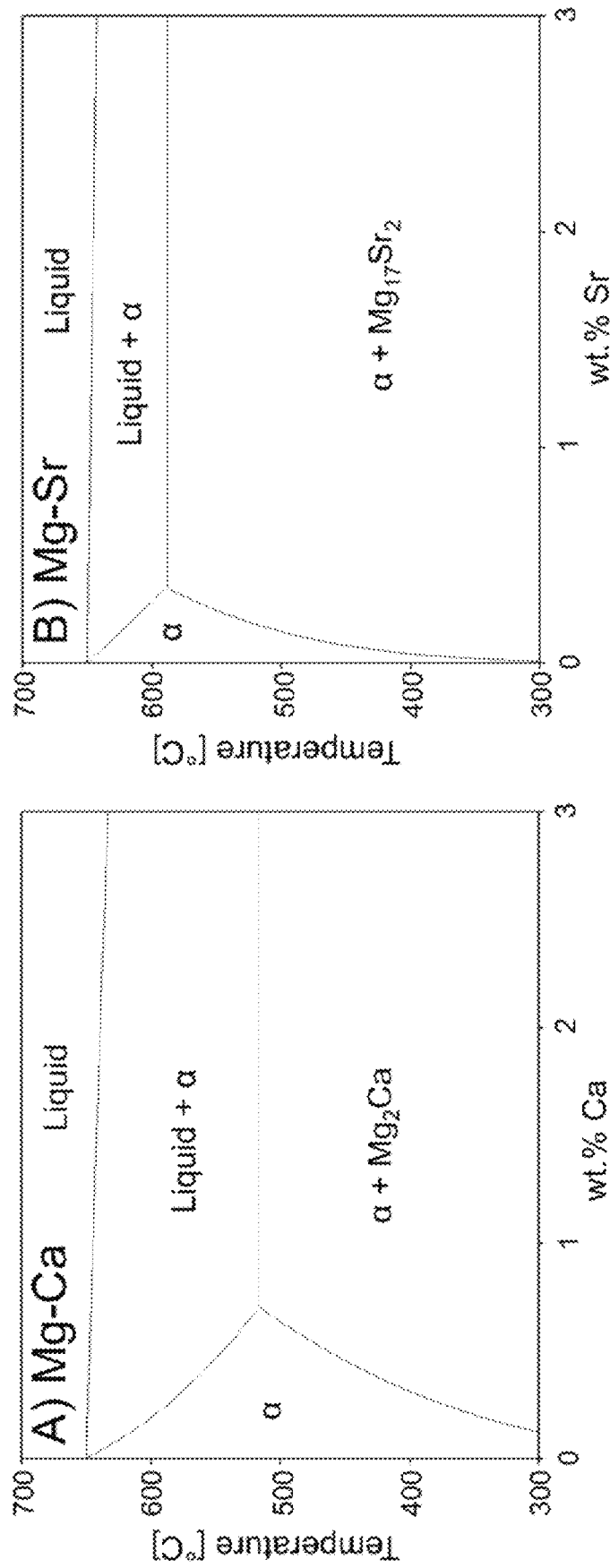

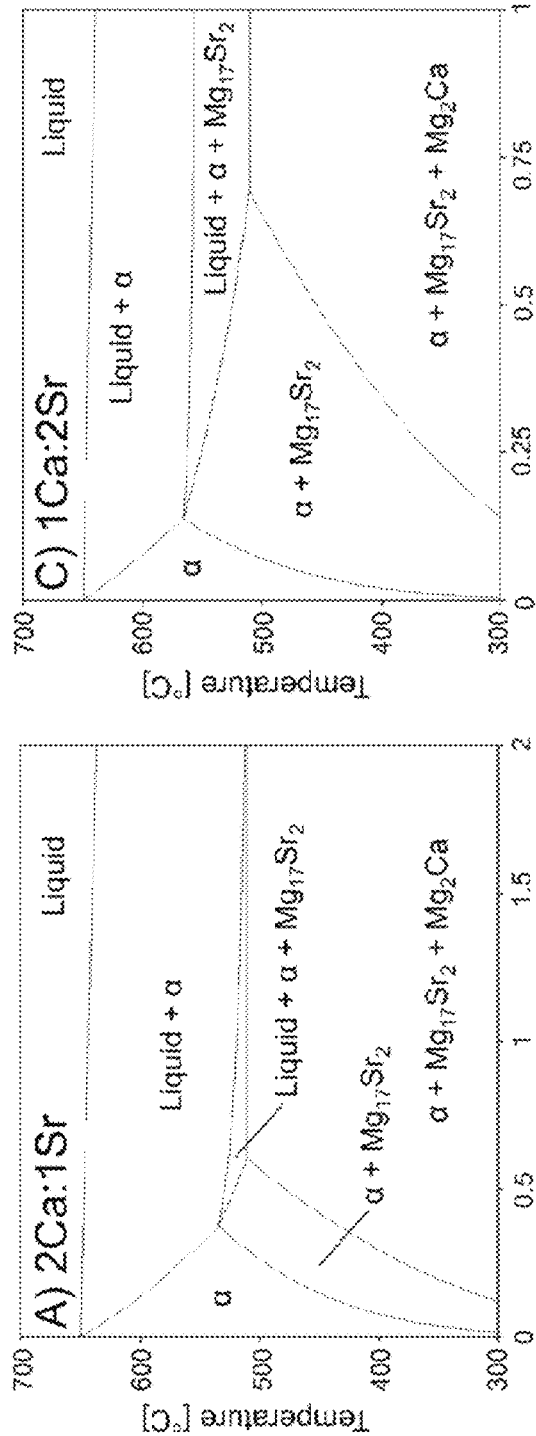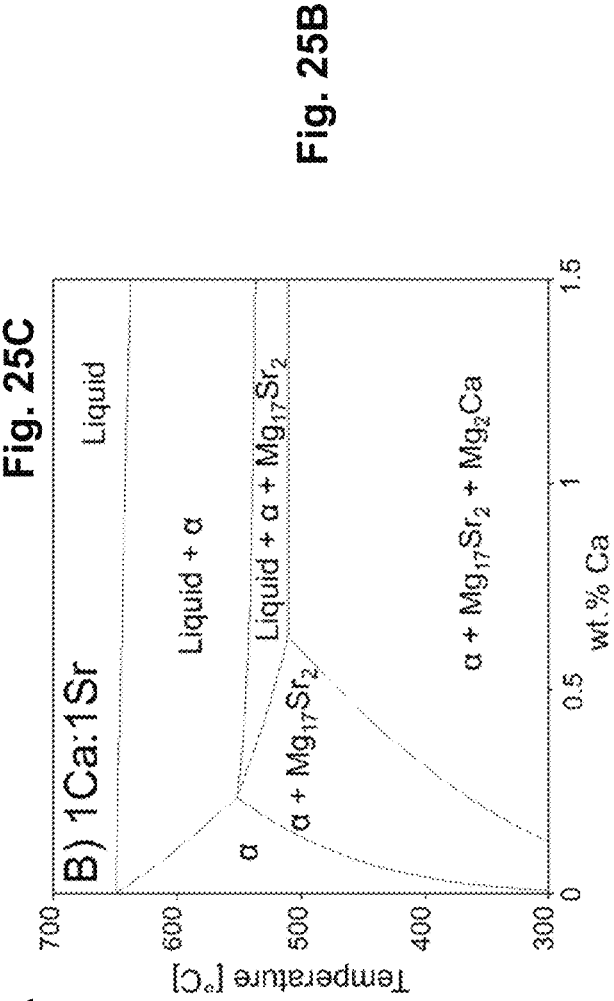
Fig. 25A
Fig. 25B
Fig. 25C

BIORESORBABLE METAL ALLOY AND IMPLANTS

CROSS-REFERENCE TO RELATED APPLICATIONS

This application is a continuation application of U.S. application Ser. No. 15/381,163 filed on Dec. 16, 2016, entitled "BIORESORBABLE METAL ALLOY AND IMPLANTS MADE OF SAME", which is a continuation-in-part application of U.S. application Ser. No. 13/808,037 filed on Jun. 7, 2013 entitled "BIORESORBABLE METAL ALLOY AND IMPLANTS MADE OF SAME", which is the 35 U.S.C. § 371 national stage of PCT application having serial number PCT/US11/42892, filed on Jul. 2, 2011, where the PCT application also claims priority to U.S. provisional application having Ser. No. 61/361,327 filed on Jul. 2, 2010, each of which is entirely incorporated herein by reference.

STATEMENT REGARDING FEDERALLY SPONSORED RESEARCH OR DEVELOPMENT

This invention was made with Government support under 1520252 awarded by the National Science Foundation. The Government has certain rights in this invention.

BACKGROUND

Biomaterials are used in numerous medical applications today, such as fixation devices, replacements and surgical equipment. Implants are typical examples of a biomaterial application and there are several different implant materials used today. Many of these are however designed to stay in the body permanently even though they only serve their function temporarily. Even if the materials are biocompatible there are several complications associated with long term presence of implants, including allergy and sensitization. Many of these implants are only left in the body to eliminate risks concerning the removal process. Removing an implant usually involves surgery which increases both cost and patient morbidity. These negative consequences would be eliminated by using a biodegradable material. A completely biodegradable implant would dissolve and be absorbed by the body after the healing process is completed. Commonly used metallic implant materials include stainless steels, titanium alloys and cobalt-chromium alloys. These materials have great mechanical properties and are often used in load bearing applications. The mechanical properties of some common alloys can be seen in Table 1. However, many metallic corrosion products are harmful to the body and none of the implant metals used are biodegradable. Ceramic materials are known for their high strength and are generally biocompatible. Synthetic hydroxyapatite and other calcium phosphates as well as bioactive glass are commonly used materials for bone augmentation and bone replacement. They resemble the bone structure which gives good chemical bonding to bone and is therefore defined as bioactive. Alumina and zirconia are commonly used inert biomaterials. Ceramic coatings are frequently used on metallic implants to increase the biocompatibility and to induce bone ingrowth. The biggest disadvantage of ceramics is a general lack of ductility, which make them susceptible to catastrophic brittle fracture. There are numerous polymeric biomaterials used today, such as polyethylene (PE), polyvinylchloride (PVC), poly(methyl methacrylate) (PMMA) etcetera. However, all polymers have the disadvantage of low strength which eliminates their possibility to be used in load bearing applications, such as for example bone fixation devices.

TABLE 1

Mechanical properties of magnesium, human bone and some commonly used biomaterials. The ranges of values are depend on testing conditions and/or anatomical location.

| | Elastic modulus (GPa) | Density (g/cm³) | Yield strength (MPa) | Tensile strength (MPa) |
|---|---|---|---|---|
| Magnesium | 45[1] | 1.74[1] | 70[2] | 176[2] |
| Human cortical bone | 5-23[3] | 1.8-2.0[3] | 106.224[4] (compressive) | 51.72[4] |
| Stainless steel | 190[5] | 8.0[3] | 300-1200[5] | 480-620[3] |
| Ti6Al4 | 144[1] | 4.43[1] | 896[1] | 1000[1] |
| Alumina | 380[4] | 3.95[6] | 2260-2600[6] | 270[4] |
| Bioactive glass | 35[3] | — | — | 40-200[2,3] |
| Synthetic hydroxyapatite | 73-117[7] | 3.1[7] | 600[7] (compressive) | 0.7[7] |
| Biodegradable PGA | 12.8[8] | 1.5[9] | — | 339-394[9] |
| Biodegradable L-PLA | 1.2-3[4] | — | — | 28-48[4] |

References are compiled from different sources;
[1](ASM-International 1999),
[2](Cardarelli 2008),
[3](Witte, Hort et al. 2008),
[4](Kutz 2002),
[5](Bartel, Davy et al. 2006),
[6](Harper 2001),
[7](Staiger, Pietak et al. 2006),
[8](Maurus and Kaeding 2004),
[9](Brandrup, Immergut et al. 2005).

SUMMARY

Embodiments of the present disclosure provide for structures including an alloy of calcium, strontium, and magnesium.

An embodiment of the present disclosure includes a structure including an alloy having: about 0.3 to 2 weight percent calcium; about 0.3 to 2 weight percent strontium; and about 96 to 99.4 weight percent magnesium.

In another embodiment, the structure includes the alloy having: about 0.6 to 2 weight percent calcium; about 0.6 to 2 weight percent strontium; and about 96 to 98.8 weight percent magnesium.

In another embodiment, the structure includes the alloy where the weight percent of calcium is about 1.5 to 2 weight percent, where the weight percent of strontium is about 1.5 to 2 weight percent, and where the weight percent of magnesium is about 96 to 97 weight percent.

In another embodiment, the structure includes the alloy where the weight percent of calcium is about 0.6 to 1.5 weight percent, where the weight percent of strontium is about 0.6 to 1.5 weight percent, and where the weight percent of magnesium is about 97 to 98.8 weight percent.

In an embodiment, the structure can be a spinal implant (e.g., a cage, dowel or wedge, or a rod, screw, pin or plate) or a dental implant.

In an embodiment, the structure can be a cannulated screw for femoral head fixation, fracture fixation screw and plate system for use in various extremity locations, suture anchor, interference screw, surgical clip, and vascular stent, and the like.

In an embodiment, the structure can be a prosthetic femoral hip joint; a prosthetic femoral head; a prosthetic acetabular cup; a prosthetic elbow; a prosthetic knee; a prosthetic shoulder; a prosthetic wrist; a prosthetic ankle; a prosthetic hand; a prosthetic finger; a prosthetic toe; a prosthetic vertebrae; a prosthetic spinal disc; a prosthetic cochlea; a prosthetic vessel; or a prosthetic heart valve.

BRIEF DESCRIPTION OF THE DRAWINGS

The advantages of embodiments of the present disclosure will be apparent upon consideration of the following detailed disclosure, especially when taken in conjunction with the accompanying drawings wherein:

FIGS. 3A-C are XRD patterns of (FIG. 3A) Mg-0.5Ca-0.5Sr alloy, (FIG. 3B) Mg-1.0Ca-0.5Sr alloy, and (FIG. 3C) Mg-1.0Ca-1.0Sr alloy samples. All three alloys display the same phases: α-Mg, $Mg_2Ca$ and $Mg_{17}Sr_2$.

FIG. 6 is an SEM image and an XRD pattern of the corroded surface of Mg-1.0Ca-1.0Sr alloy. The amount of corrosion products on the surface is significantly greater than that of Mg-1Ca-0.5Sr. The corrosion products, microcracks and holes in the surface layer are labeled. It can be seen that the holes run deep through the surface layer and can assist in the flow of media to unprotected surface beneath the corrosion layer. The XRD shows the presence of $Mg(OH)_2$ and $(Mg,Ca)_3(PO_4)_2$ phosphate on the surface of the corroded sample.

FIG. 16A plots calculated particle volume percent vs. calculated fraction of $Mg_{17}Sr_2$ of the total precipitate volume ($Mg_{17}Sr_2+Mg_2Ca$) for different alloying addition wt. %. FIG. 16B plots degradation rate as a function of $Mg_{17}Sr_2$ fraction and alloy addition wt. %.

FIGS. 24A-B are binary phase diagrams up to 3% alloying addition of FIG. 24A) Mg—Ca and FIG. 24B) Mg—Sr.

FIGS. 25A-C are pseudobinary diagrams up to 3 wt. % alloying addition with stoichiometry as indicated. Note that the x-axis only tracks wt. % Ca, with wt. % Sr implied.

DETAILED DESCRIPTION

Figure 1A:
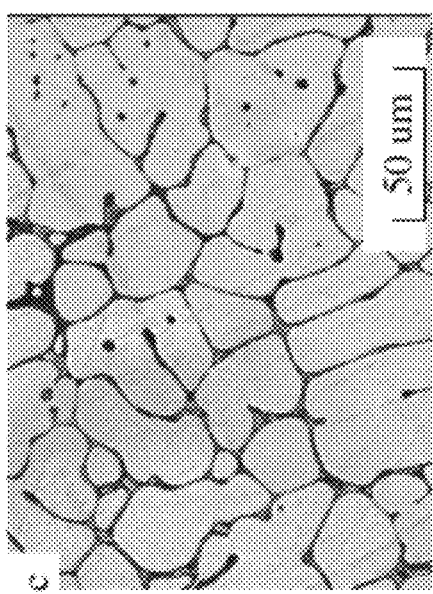
FIGS. 1A-E are optical micrographs of (FIG. 1A) Mg-0.5Ca-0.5Sr alloy, (FIG. 1B) Mg-1.0Ca-0.5Sr alloy, (FIG. 1C) Mg-1.0Ca-1.0Sr alloy, (FIG. 1D) Mg-1.0Ca-2.0Sr alloy, and (FIG. 1D) Mg-7.0Ca-3.5Sr alloy samples. The alloys show the characteristic dendritic structure associated with as-cast alloys. The light regions are α-Mg dendrites whereas the dark regions are mixtures of Ca and Sr-rich intermetallics in eutectic structure.
Figure 1B:
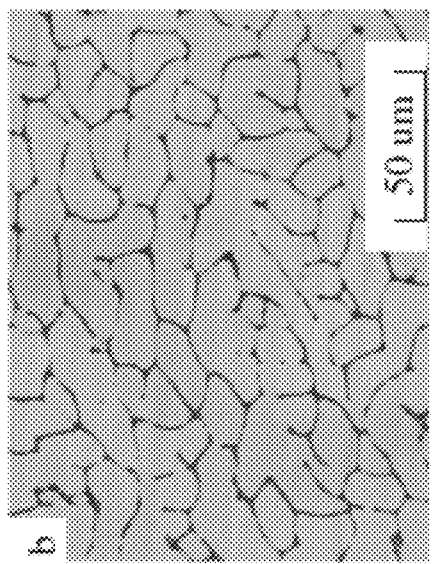
Figure 1C:
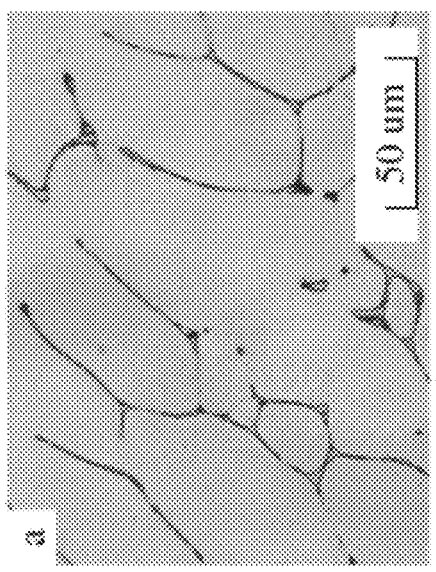
Figure 1D:
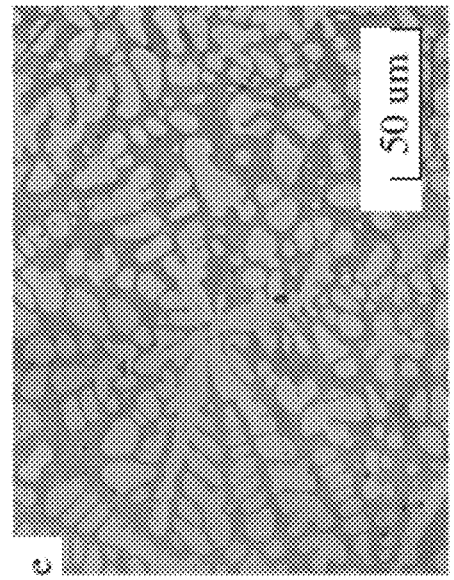
Figure 1E:
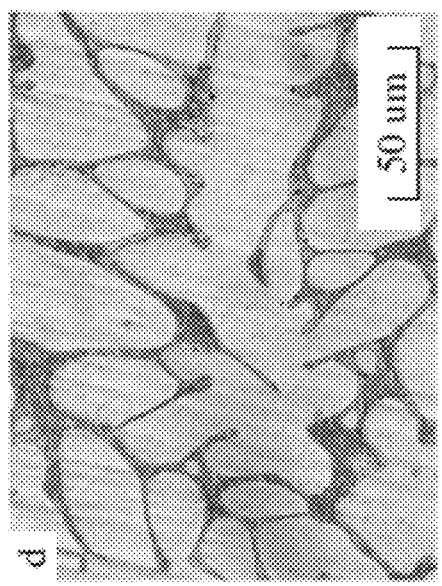

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method may be carried out in the order of events recited or in any other order that is logically possible.

Embodiments of the present disclosure will employ, unless otherwise indicated, techniques of chemistry, material science, biology, and the like, which are within the skill of the art. Such techniques are explained fully in the literature.

Prior to describing the various embodiments, the following definitions are provided and should be used unless otherwise indicated.

Unless otherwise defined, all technical and scientific terms used herein have the same meaning as commonly understood by one of ordinary skill in the art of chemistry, physics, fluid dynamics, and the like. Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DISCUSSION

Embodiments of the present disclosure provide for structures including an alloy of calcium, strontium, and magnesium. The structure can be made completely of the alloy or a portion of the structure can be made of the alloy. In an embodiment the structure can be an implant such as an orthopedic implant, a dental implant, or the like.

There is no material used today that has the strength of a metal or ceramic material as well as biodegradable properties. Magnesium is potentially an excellent implant material due to its attractive mechanical properties and non-toxicity. It has a high corrosion rate, especially in chloride containing solutions, which means that it will degrade in the human body. If the corrosion rate can be controlled the material is a great candidate for use as a biodegradable implant.

Magnesium alloys currently under investigation by researchers in the field for biomedical applications were originally designed for automotive and aerospace components with little consideration for their biocompatibility. As a result, most of the alloys currently being investigated contain toxic alloying elements. Embodiments of the present disclosure provide for a degradable implant material selecting the alloying elements for purposes of obtaining optimal mechanical functionality while maintaining biocompatibility. Calcium is an essential element for the human body and is non-toxic. Strontium is present in human bones and has been shown to promote osteoblast function and increase bone formation when added to hydroxyapatite, as compared to pure hydroxapatite. This creates the opportunity to develop metals that can completely dissolve within the body and that release dissolution products that are 100% biocompatible and enhance the biological processes in bone. In addition to their biological response, calcium and strontium are known to strengthen magnesium alloys while increasing their corrosion resistance. Controlling these elements and the corresponding microstructures that develop upon processing, our magnesium-based alloy can be designed with controllable degradation rates and mechanical properties. Hence, the inventors have shown that the magnesium-based alloy system containing calcium and strontium will produce promising results.

Embodiments of the present disclosure provide for magnesium alloys that can be used in biomedical implant materials which will be advantageous over other materials as they can dissolve completely in the human body, while exhibiting the other desirous attributes of metal materials. The development of the alloy embodiments, has now enabled the development of medical devices that do not need additional surgeries for their removal. This greatly reduces the cost of treatment and patient morbidity. A magnesium-based alloy containing calcium and strontium is an improvement over other magnesium alloy systems being investigated as both calcium and strontium are elements present in bones and are biocompatible whereas the alloying elements being used in other studies are toxic. Thus, using magnesium alloy containing calcium and strontium greatly reduces the risk of potential toxicity by the degradation products being released from the medical device.

The present disclosure and examples therein measure the degradation properties of alloys in the Mg-rich corner of the Mg—Ca—Sr ternary phase diagram and analyze parameters that can determine degradation rate in this system. As discussed in detail in Example 14, a survey of 18 Mg—Ca—Sr ternary, along with Mg—Ca and Mg—Sr binary, alloys has been conducted. The survey demonstrated that there are significant non-linear effects on degradation upon mixing alloying elements, which are shown to be most accurately predictable by eutectic contiguity, as measured by eutectic microconstituent triple point density and the mechanism was confirmed with subsurface imaging techniques. Solidification microstructure in these alloys is a direct consequence of the ratio of alloying elements, which is not predictable based only on the binary studies. These results demonstrate that the combination of Sr and Ca in Mg lead to a controllable cast microstructure, having direct impact on the degradation rate of the ternary alloy. Between Mg—Ca and Mg—Sr binary systems, there are non-linear solidification effects on microstructure contiguity, unpredictable by interpolation of the alloys.

In an embodiment, the alloy can include, by weight percentage, about 0.3 to 10 percent calcium; about 0.3 to 10 percent strontium; and about 50 to 99.5 percent magnesium. In an exemplary embodiment, the alloy comprises about 0.7 to 8 percent strontium. In a more specific embodiment, the alloy comprises about 1 to 5 percent strontium. In an embodiment, the alloy can include about 0.6 to 2 weight percent of calcium, about 0.6 to 2 weight percent of strontium, and about 96 to 98.899.4 weight percent of magnesium. In another embodiment, the alloy can include about 0.3 to 2 weight percent of calcium, about 0.3 to 2 weight percent of strontium, and about 96 to 99.4 weight percent of magnesium. In an embodiment, the alloy can include about 0.6 to 1.5 weight percent of calcium, about 0.6 to 1.5 weight percent of strontium, and about 97 to 98.8 weight percent of magnesium. In an embodiment, the alloy can include about 1.5 to 2 weight percent of calcium, about 1.5 to 2 weight percent of strontium, and about 96 to 97 weight percent of magnesium. Additional details regarding these amounts are discussed in more detail in Example 14 and the corresponding figures.

According to certain embodiments, embodiments of the present disclosure relate to a bioresorbable, non-toxic, osteogenic magnesium alloy. As used herein, the term osteogenic relates to the property of facilitating in growth of bone (osteoconductivity) and/or promoting new bone growth (osteoinductivity).

According to another embodiment, embodiments of the present disclosure pertain to a non-toxic, non-immunoreactive orthopedic implant comprised of a magnesium alloy that comprises calcium and strontium. In an embodiment, the present disclosure can have antimicrobial attributes. The implant may be a composite where only a portion includes the magnesium alloy. In a more specific embodiment, the alloy comprises about 50 or more percent total weight of the implant. There are numerous configurations that the implant may take for use in orthopedic type surgeries, including but not limited to, a spinal cage, a dowel, a wedge, a rod, a plate, a screw, a pin or a plate. In an embodiment, the structure can be a cannulated screw for femoral head fixation, fracture fixation screw and plate system for use in various extremity locations, suture anchor, interference screw, surgical clip, or vascular stent, and the like.

In alternative embodiment, embodiments of the present disclosure relate to an alloy that comprises magnesium, calcium and strontium and which is substantially free from aluminum, manganese, zirconium and/or zinc. As used herein, the term "substantially free" means that the element or compound comprises less than 3 percent by weight of the alloy.

In yet another embodiment, a biomaterial is disclosed that comprises a magnesium alloy at least 50% by weight. A biomaterial comprising a magnesium alloy at least 50% by weight includes a biomaterial which comprises a magnesium alloy at least 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% by weight, or a magnesium alloy 100% by weight.

According to another embodiment, the embodiments of the present disclosure related to an implant to be positioned in vivo during surgery, especially orthopedic surgery to replace a joint, such as, for example, a knee joint or a hip joint. Thus, the implant can be used in a method for orthopedic surgery that includes surgically positioning the implant within a vertebrate in need thereof. If bone growth is facilitated, the implant can be termed part of an osteoconductive process that includes contacting a bone under in vivo conditions with the implant.

According to another embodiment, a magnesium alloy embodiment is used to coat an orthopedic or dental implant.

According to further embodiment, a dental implant embodiment is comprised of, at least partially, a magnesium alloy as taught herein.

EXAMPLES

Example 1: Alloy Preparation

In this study, five different Mg—Ca—Sr alloys with targeted compositions of Mg-0.5Ca-0.5Sr, Mg-1.0Ca-0.5Sr, Mg-1.0Ca-1.0Sr, Mg-1.0Ca-2.0Sr and Mg-7.0Ca-3.5Sr were prepared using high purity Mg chips (99.98%, Sigma-Aldrich, St. Louis, MO), Ca granules (99.5%, Alfa-Aesar, Ward Hill, MA) and Sr granules (99%, Sigma-Aldrich, St. Louis, MO). Melting of the alloys was carried out between 725-825° C. in high purity graphite crucibles. Each melt was held for approximately 40 min and stirred prior to pouring. The melt was then poured into high purity graphite moulds that were allowed to air-cool to room temperature. A protective argon atmosphere was maintained throughout the melting and casting process. The compositions of the as cast alloys were determined using inductively coupled plasma-atomic emission spectrometry (ICP-AES). The nominal and actual compositions of the investigated Mg alloys are listed in Table 2.

TABLE 2

Nominal and analyzed compositions of Mg—Ca—Sr alloys

| | Mg (wt %) | | Ca (wt %) | | Sr (wt %) | |
|---|---|---|---|---|---|---|
| | Nominal | Analyzed | Nominal | Analyzed | Nominal | Analyzed |
| Mg-7.0Ca-3.5Sr | 90 | 89.13 | 7 | 7.32 | 3.5 | 3.55 |
| Mg-1.0Ca-2.0Sr | 97 | 96.93 | 1 | 1.18 | 2 | 1.89 |
| Mg-1.0Ca-1.0Sr | 98 | 97.99 | 1 | 1.21 | 1 | 0.80 |
| Mg-1.0Ca-0.5Sr | 98.5 | 98.24 | 1 | 1.29 | 0.5 | 0.47 |
| Mg-0.5Ca-0.5Sr | 99 | 98.96 | 0.5 | 0.55 | 0.5 | 0.49 |

Example 2: Microstructural Characterization

For microscopic evaluation, the samples were ground with silicon carbide (SiC) emery papers to 4000 grit, and polished to 0.3 micron using a colloidal silica suspension. The polished samples were etched using acetic picral as an etchant. The microstructural analysis was performed using light optic microscopy (LOM, Olympus PME3) and scanning electron microscopy (SEM, JEOL JSM 6400). Energy-dispersive X-ray spectroscopy (EDS, JEOL JSM 6400) and XRD (Phillips APD 3720) was employed to identify the different phases present in the alloys and the corroded surfaces.

Example 3: Immersion Tests

The samples were ground to 320 grit using SiC emery paper and then cleaned with ethanol. The immersion test was carried out at 37° C. in Hanks balanced salt solution containing 0.185 g/l $CaCl_2.2H_2O$, 0.40 g/l KCl, 0.06 g/l $KH_2PO_4$, 0.10 g/l $MgCl_2.6H_2O$, 0.10 g/l $MgSO_4.7H_2O$, 8.00 g/l NaCl, 0.35 g/l $NaHCO_3$, 0.48 g/l $Na_2HPO_4$, 1.0 g/l D-Glucose (Thermo Scientific Inc., Waltham, MA). The ratio of Hanks solution to the surface area of the samples was kept approximately 150. The high value was chosen to minimize the change in pH value during the experiment. The hydrogen evolution was measured by placing the samples at the bottom of a beaker with a funnel and a measuring cylinder placed on top of the beaker to collect and measure the volume of hydrogen gas evolved. The gas volume was measured every 24 h up to 8 days. The tests were performed in triplicates and the average of the data is reported.

Example 4: Compression Test

Compression testing of the alloys was carried out with an Instron 5582 universal testing machine. The compression samples were machined from as cast cylindrical rods. Each sample had a diameter of 6 mm and length of 9 mm. Compression tests were performed at a constant compression strain rate of 1% per min. Three compression samples were tested for each composition and the mean of the values are reported in Table 4.

Example 5: Cytotoxicity Evaluation

Toxicity testing was carried out on alloy extracts. Alloy samples were polished using 4000 grit paper and then sterilized by rinsing in ethanol and incubating under ultraviolet light for 15 min. The samples were put in a 50 ml conical tube and incubated in 1 ml of culture media per $cm^2$ of metal surface area, for 72 h at 37° C. in a humidified atmosphere of 5% $CO^2$ in air. The culture media consisted of α-minimal essential medium (α-MEM) supplemented with 10% fetal bovine serum, 1% L-glutamine, 1% pyruvate and 1% penicillin/streptomycin (Thermo Scientific Inc., Waltham, MA). After 72 h, alloy samples were removed from the conical tube and the alloy extracts were filtered through a 0.22 μm pore size filter and then serially diluted to make 50% and 10% concentrates with the fresh culture media. The diluted extraction media were refrigerated at 4° C. until utilized. The composition of the dissolved ions in the culture media and alloy extracts was measured using ICP. X-ray Diffraction was employed for characterization of the degradation products on the surface of the samples after immersion.

MC3T3-E1 mouse osteoblastic cell line was utilized for experiments and cells were cultured in α-MEM differentiation media using standard procedures. The control groups used untreated cells in culture media as the negative control and cells treated with 1% triton X-100 in culture media as the positive control. Cells were incubated in 24-well polystyrene plates at a density of 1×106 cells per well and incubated for 24 h to allow attachment. The media was then replaced with 1 ml of extraction media per well. The LDH cytotoxicity detection assay (Roche Applied Sciences) was performed on the extraction media as per the manufacturer's protocol at 3 and 5 days of culture and measured spectrophotometrically at 490 nm (Victor 3 and Wallac 1420, PerkinElmer, Waltham, MA). The supernatant was replaced with fresh extraction media on the end of day 3 upon collection of the extraction media. The medium pH was not adjusted during the tests. Statistical analyses were performed using general linear nested model ANOVA with Systat statistical software (Version 12, Systat Software, San Jose, CA) and significant differences were obtained using Tukey's honestly significant difference test. The data was pooled from 3 different experiments with n of ≥9.

The following examples relate to Examples 1-5 above

Example 6: Alloy Microstructural Characterization

FIGS. 1A-E show the optical micrographs of the five alloys. All alloys morphologically display large irregular, ellipsoidal-shaped α-Mg phase dendrites and intermetallic compounds in the interdendritic regions. Except Mg-0.5Ca-0.5Sr, all of the alloys have a continuous precipitate and eutectic network along the dendrites. Since Mg-7.0Ca-3.5Sr and Mg-1.0Ca-2.0Sr showed low corrosion resistance and dissolved quickly (see next section), thus they were excluded from any further microstructural analysis. FIGS. 2A-F shows the SEM images of the microstructure of Mg-0.5Ca-0.5Sr, Mg-1.0Ca-0.5Sr, and Mg-1.0Ca-1.0Sr alloys. It can be seen that the dendrite spacing of Mg-0.5Ca-0.5Sr is relatively larger than that of Mg-1.0Ca-0.5Sr and Mg-1.0Ca-1.0Sr. It can be seen that with an increase in Ca and Sr contents, the amount of intermetallic compounds along the dendrite boundaries increases. Quantitative analysis was performed using EDS to determine the approximate composition of the different phases (FIGS. 2A-C) and the results are summarized in Tables 3A-C. These intermetallic compounds were identified as Mg2Ca and Mg17Sr2 using XRD and the XRD patterns are shown in FIGS. 3A-C. It can be seen that though the amount of secondary phases present in the alloys is different, all of the alloys have the same phases present.

TABLE 3A

EDS analysis of the phases in Mg-0.5Ca-0.5Sr alloy

| | Mg (wt %) | Ca (wt %) | Sr (wt %) | 0 (wt&) |
|---|---|---|---|---|
| A | 72.2 | 3.1 | 23.5 | 1.2 |
| B | 92.6 | 4.1 | 1.5 | 1.8 |
| C | 98.6 | ≈0 | ≈0 | 1.4 |

TABLE 3B

EDS analysis of the phases in Mg-1.0Ca-0.5Sr alloy

| | Mg (wt %) | Ca (wt %) | Sr (wt %) | 0 (wt&) |
|---|---|---|---|---|
| A | 72.2 | 3.1 | 23.5 | 1.2 |
| B | 92.6 | 4.1 | 1.5 | 1.8 |
| C | 98.6 | ≈0 | ≈0 | 1.4 |

EDS analysis of the phases in Mg-0.5Ca-1.0Sr alloy

| | Mg (wt %) | Ca (wt %) | Sr (wt %) | 0 (wt&) |
|---|---|---|---|---|
| A | 71.74 | 7.55 | 19.7 | 1.01 |
| B | 86.15 | 7.97 | 4.56 | 1.32 |
| C | 99.07 | 0.48 | ≈0 | 0.45 |

Example 7: Immersion Test

Figure 4:
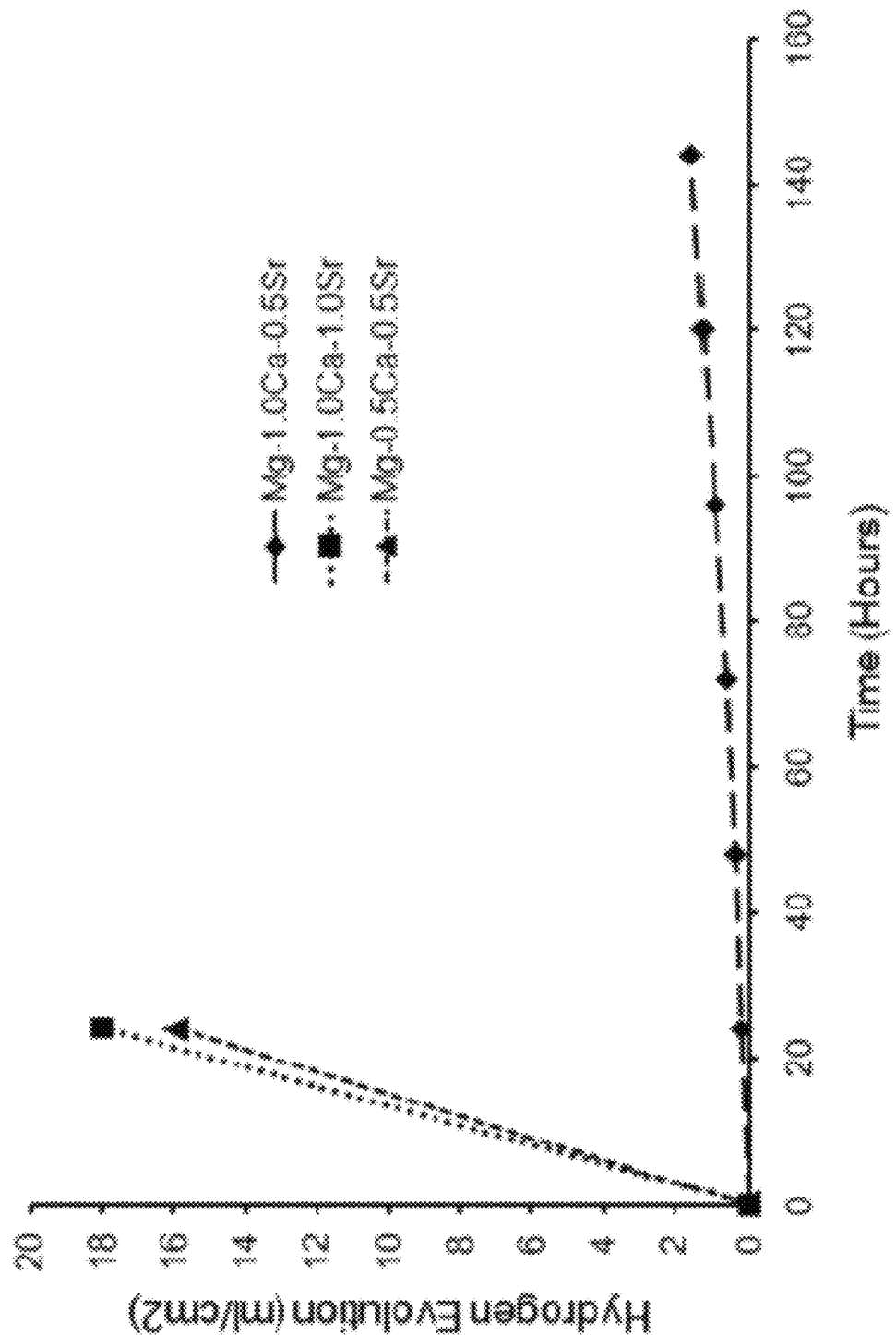
FIG. 4 shows hydrogen evolution volumes of alloys immersed in Hank's solution.
Figure 5:
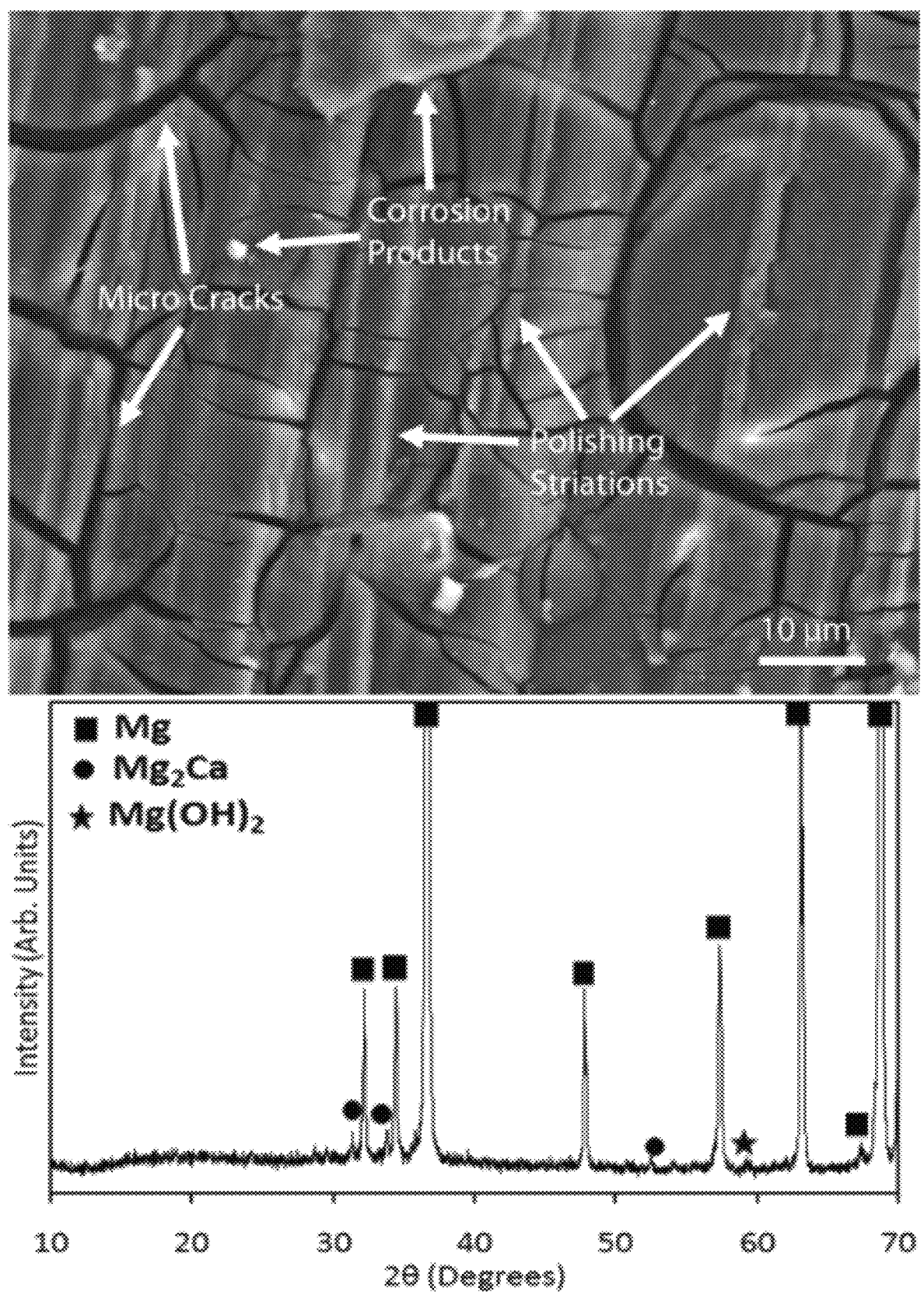
FIG. 5 is an SEM image and an XRD pattern of the corroded surface of Mg-1.0Ca-0.5Sr alloy. The large striations on the surface of the samples are due to polishing effects during sample preparation. The microcracks, striations and corrosion products are labelled accordingly. It is apparent in this figure there is a significant number of microcracks forming on the sample surface.
Figure 7:
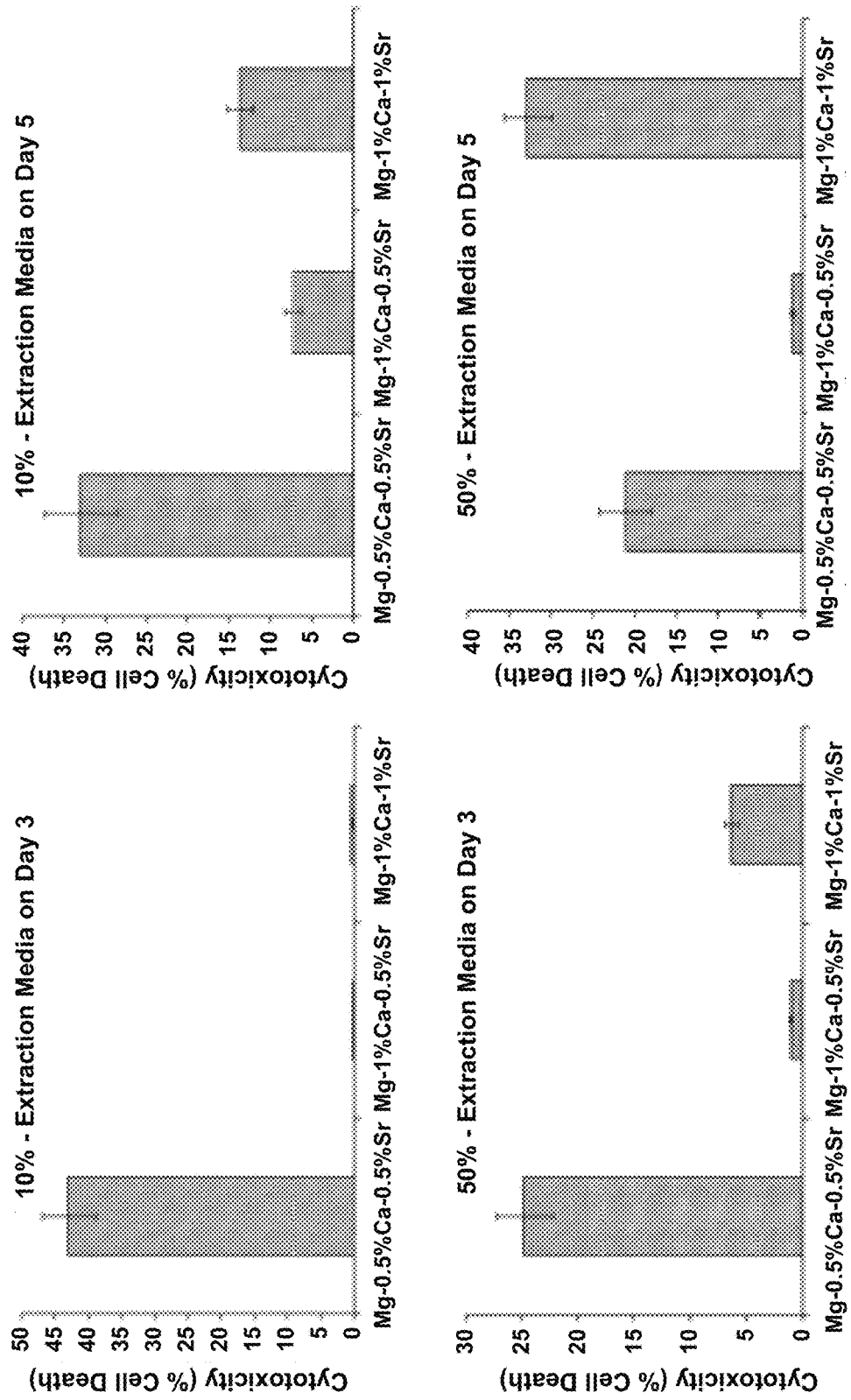
FIG. 7 shows toxicity on MC3T3-E1 cells expressed as a percentage of dead cells for different alloys after culturing in 10% alloy extraction media on day 3, 10% alloy extraction media on day 5, 50% alloy extraction media on day 3, and 50% alloy extraction media on day 5.
Figure 8C:
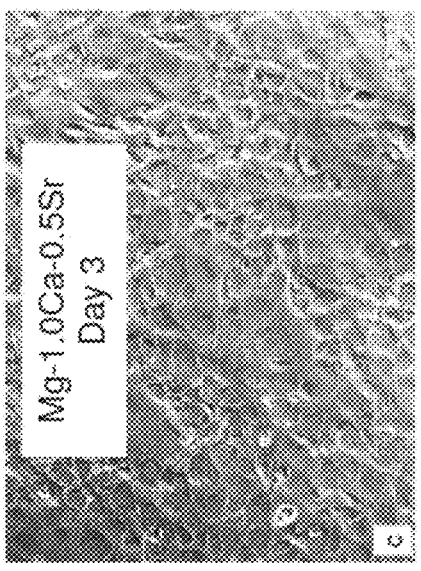
FIGS. 8A-F are Optical Morphologies of MC3T3-E1 cells cultured in 50% concentration of (FIGS. 8A-B) Mg-0.5Ca-0.5Ca (FIGS. 8C-D) Mg-1.0Ca-0.5Sr and (FIGS. 8E-F) Mg-1.0Ca-1.0Sr alloy extracts respectively, after 3 and 5 days of culturing.
Figure 8B:
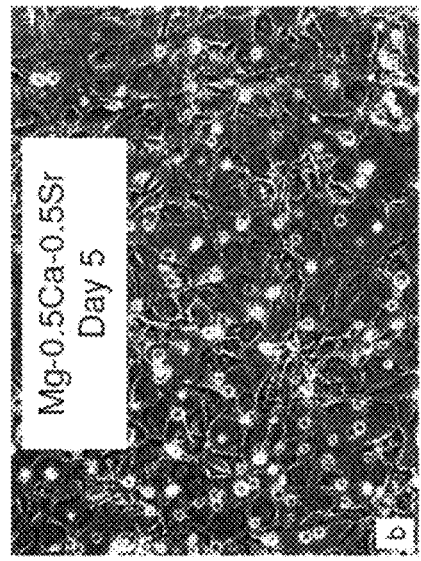
Figure 8A:
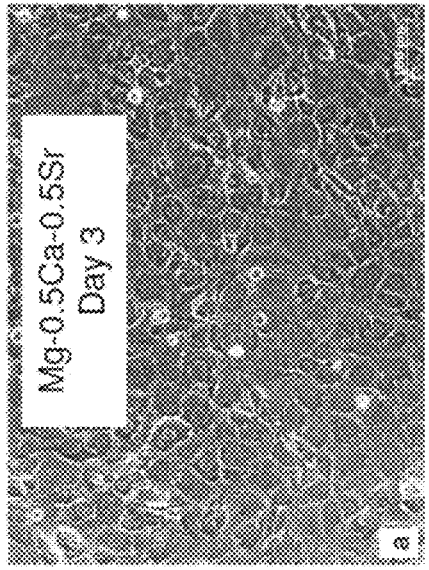
Figure 8F:
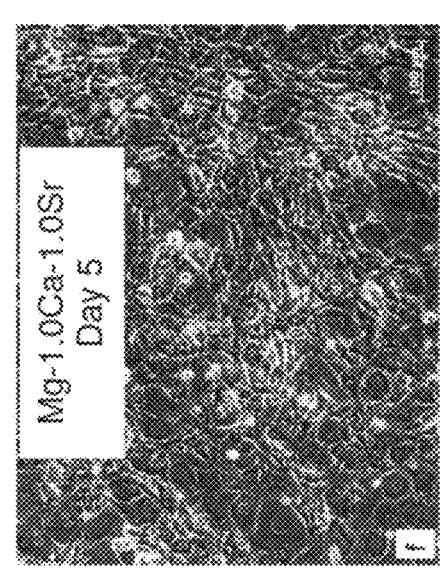
Figure 8E:
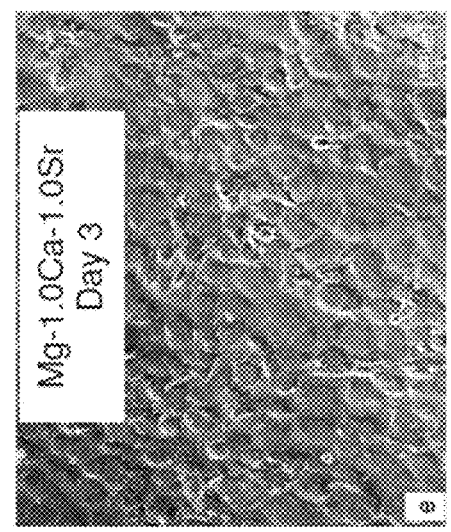
Figure 8D:
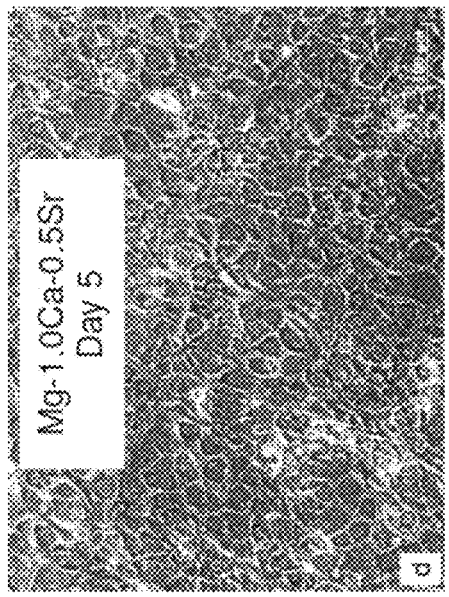

The results of the hydrogen evolution test can be seen in FIG. 4. The alloys with high amounts of alloying additions, Mg-7.0Ca-3.5Sr and Mg-1.0Ca-2.0Sr, are not shown due to their rapid corrosion rate. These alloys completely dissolved and disintegrated within the first 24 h of immersion, thus surface area in contact with the Hanks solution could not be calculated. It can be seen that Mg-1.0Ca-1.0Sr and Mg-0.5Ca-0.5Sr alloys also show rapid degradation. The alloy with the slowest degradation rate was Mg-1.0Ca-0.5Sr. This alloy demonstrated a significantly lower hydrogen evolution of approximately 0.01 ml/cm2/h. This is much lower than that of traditional Mg alloys like AZ91 and ZE41.13 It was also observed that the degradation was more rapid in the beginning, followed by stabilization of the corrosion rate. FIG. 5 shows the SEM image and XRD pattern of the corroded surface of Mg-1.0Ca-0.5Sr alloy after three days of immersion in culture media according to the extraction process mentioned under the toxicity test section. It can be observed that scratches from polishing are still visible, implying that there is no significant corrosion of the surface or minimal deposition of corrosion products on the surface.

FIG. 6 shows the Mg-1.0Ca-1.0Sr alloy under similar conditions. Mg-0.5Ca-0.5Sr showed corrosion behavior similar to Mg-1.0Ca-1.0Sr and is hence not shown here. The SEM micrograph shows severe corrosion and significant deposition of corrosion products on the surface of the alloy. The XRD images in FIGS. 5 and 6 show that in both the alloys, $Mg(OH)_2$ is present on the surface of the degrading samples. For the Mg-1.0Ca-1.0Sr alloy sample, $(Mg,Ca)_3(PO_4)_2$ is also observed in the corrosion layer.

Example 8: Compression Test

Mechanical properties of the alloys are enumerated in Table 4. Compressive strength of Mg-0.5Ca-0.5Sr alloy and Mg-1.0Ca-0.5Sr alloy is similar whereas the strength of Mg-1.0Ca-1.0Sr alloy is much lower. The mechanical properties are similar to what have been reported for binary Mg—Ca alloys with similar amounts of Ca additions (Wan Y, Xiong G, Luo H, He F, Huang Y, Zhou X. Preparation and characterization of a new biomedical magnesium-calcium alloy. Materials & Design 2008; 29:2034-2037).

TABLE 4

Mechanical properties of alloy samples.

| Alloy Composition | Compressive Strength (MPa) |
|---|---|
| Mg-0.5Ca-0.5Sr | 274.3 ± 7.2 |
| Mg-1.0Ca-0.5Sr | 274.2 ± 4.0 |
| Mg-1.0Ca-1.0Sr | 214.5 ± 3.5 |

Example 9: Cytotoxicity Evaluation

Figure 9A:
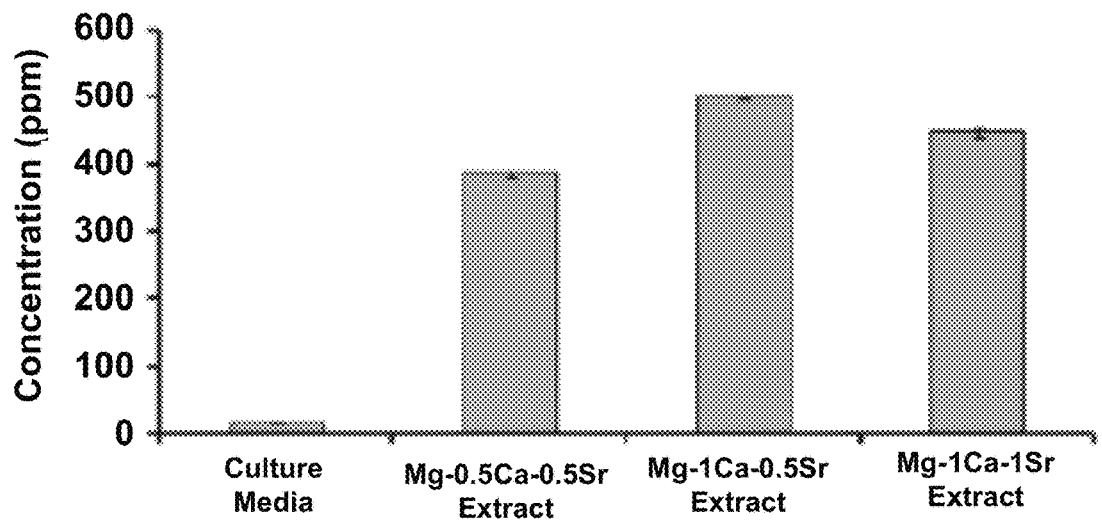
FIGS. 9A-C show alloy extract ion concentrations of (FIG. 9A) Mg, (FIG. 9B) Ca and (FIG. 9C) Sr. The columns show the average value of five measurements on each sample with error bars showing ±1 standard deviation.
Figure 9B:
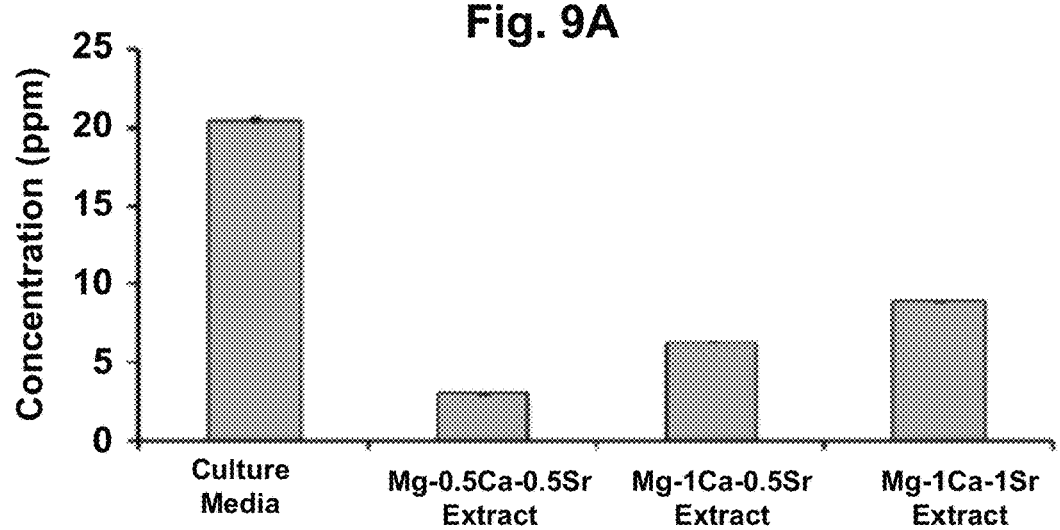
Figure 9C:
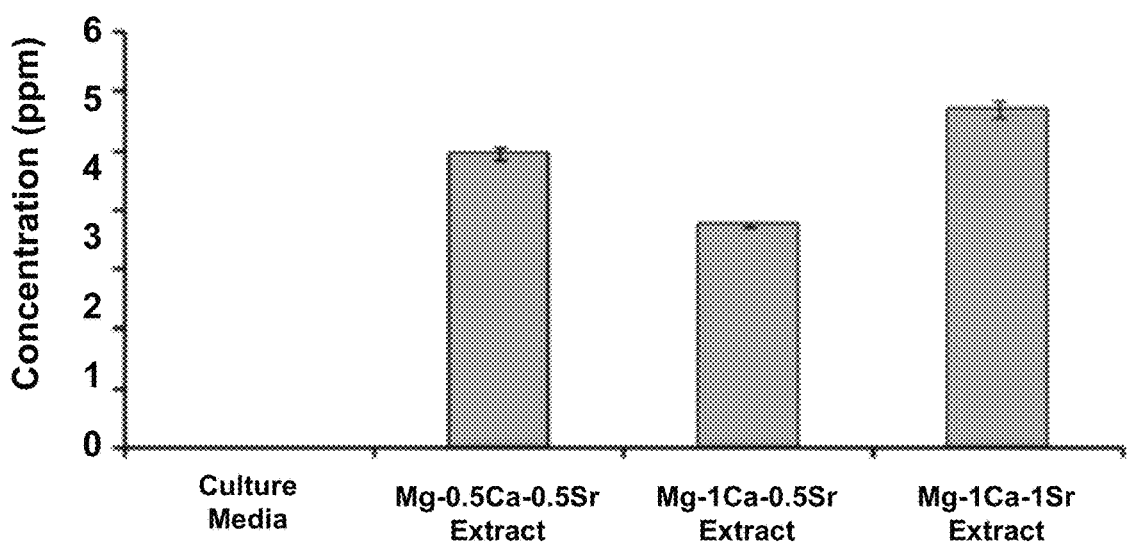

FIGS. 7A-D show differential osteoblast cytotoxic response observed upon culture of these cells with varying concentrations of Mg, Ca and Sr at different days. The bar graphs represent the average cytotoxicity of the cells in terms of percentage dead cells relative to the control, with standard error against varying alloys and concentrates on different test days. It was observed that the cytotoxicity was the least for the Mg-1.0Ca-0.5Sr alloy for all days and at different percentages of extraction media. The Mg-0.5Ca-0.5.Sr alloy extracts showed the highest cytotoxicity for all days and concentrations except for the 50% concentrate on day 5 where Mg-1.0Ca-1.0Sr alloy demonstrated higher toxicity. FIGS. 8A-F show bright field images of the cells cultured with 50% extraction media at different days. The rounded/dead cells were found to be highest for the Mg-0.5Ca-0.5Sr alloy extract, shown in FIGS. 8A-B, followed by the Mg-1.0Ca-1.0Sr alloy extract, shown in FIGS. 8E-F. The Mg-1.0Ca-0.5Sr alloy extract, FIGS. 8C-D, resulted in the least number of rounded/dead cells. The micrographs obtained via bright field imaging support the cytotoxicity data observed using LDH assay. FIGS. 9A-C shows the amount of $Mg^{2+}$, $Ca^{2+}$ and $Se^+$ ions present in the culture media and the alloy extracts. It is observed that all the extracts had a significantly high amount of $Mg^{2+}$ and $Se^+$ ions as compared to the media. However, the amount of $Ca^{2+}$ was lower than that present in the culture media.

Discussion Related to Examples 1-9

The study provided in Examples 1-9 found that the degradation rate of Mg-1.0Ca-0.5Sr alloy shows a significant improvement over that of Mg-1.0Ca binary alloy (Li Z, Gu X, Lou S, Zheng Y. The development of binary Mg—Ca alloys for use as biodegradable materials within bone. Biomaterials 2007; 29:1329-1344). The amount of hydrogen evolution is reduced by an order of magnitude as compared to results reported on cast Mg-1.0Ca alloy. This could be highly beneficial in prevention of subcutaneous gas bubbles around the implants, thereby providing a better healing environment.

There are likely two possible reasons for the improved corrosion resistance of Mg-1.0Ca-0.5Sr as compared to Mg-0.5Ca-0.5Sr and Mg-1.0Ca-1.0Sr alloys. First, the difference in the amount and nature of precipitates present and secondly, the variations in grain size influencing the degradation properties in these alloys. In the microstructures shown in FIGS. 2A-F, it can be observed that Mg-0.5Ca-0.5Sr and Mg-1.0Ca-1.0Sr contain higher amounts of the Sr-rich phase (marked A in the images) than Mg-1.0Ca-0.5Sr alloy. This observation is also in accordance with the phase fractions of different phases calculated using the PANDAT™ software system33 (CompuTherm LLC, Madison, WI) and a proprietary thermodynamic Mg database (PanMagnesium-Thermodynamic Database for commercial Magnesium Alloys. Version 7. Madison, WI: CompuTherm LLC; 2007). By using Gibbs energy minimization protocols, PANDAT is useful in calculating thermodynamic data such as phase equilibria and transformations. The presence of a higher amount of Sr-rich phase can possibly decrease the corrosion resistance of the alloy by providing an increased interface area for micro-galvanic coupling between different phases. As can be seen in the micrographs, the Mg-1.0Ca-0.5Sr alloy has significantly smaller grains than the other alloys. Overall, the enhanced corrosion resistance of Mg-1.0Ca-0.5Sr can most likely be attributed to the presence of a right balance of efficient precipitate distribution along grain boundaries and small grain size.

The formation of degradation products on the surface of the material also affects the subsequent degradation. As shown in the XRD plots in FIG. 5 and FIG. 6, $Mg(OH)_2$ is formed on the alloy surface during degradation. As the rate of hydrogen evolution for Mg-1.0Ca-0.5Sr decreases with increasing time, the $Mg(OH)_2$ layer formed on the surface seems to be protective in nature and growing with time. On the other hand, even though both $Mg(OH)_2$ and $(Mg,Ca)_3(PO_4)_2$ was found on the surface of Mg-1.0Ca-1.0Sr, the degradation layer does not seem to be protective. As observed in the SEM images, large holes leading to subsurface tunnels exist in the outer layers of the alloy. These defects, which are caused by pitting corrosion, lead to highly localized attacks that promote the flow of the media to the unprotected alloy surface, resulting in high degradation rate even after formation of a thick degradation layer.

Figure 2A:
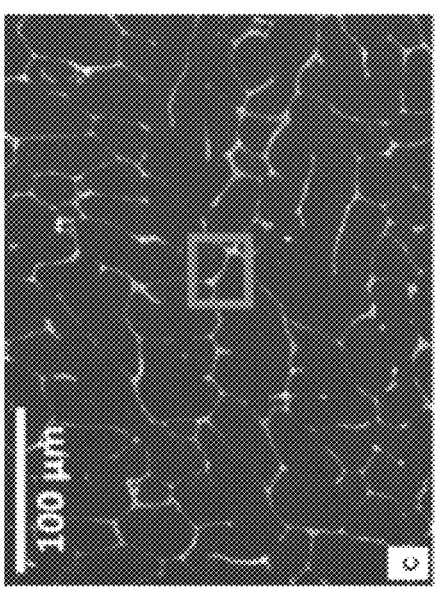
FIGS. 2A-F are SEM images of (FIG. 2A-B) Mg-0.5Ca-0.5Sr alloy, (FIGS. 2C-D) Mg-1.0Ca-0.5Sr alloy, and (FIGS. 2E-F) Mg-1.0Ca-1.0Sr alloy. The FIGS. 1B, 1D, and 1F (show the magnified images of the area in the squares and identify the phases present. Phase A is $Mg_{17}Sr_2$, Phase B is the $Mg_2Ca$ present in the eutectic and Phase C is the α-Mg phase.
Figure 2B:
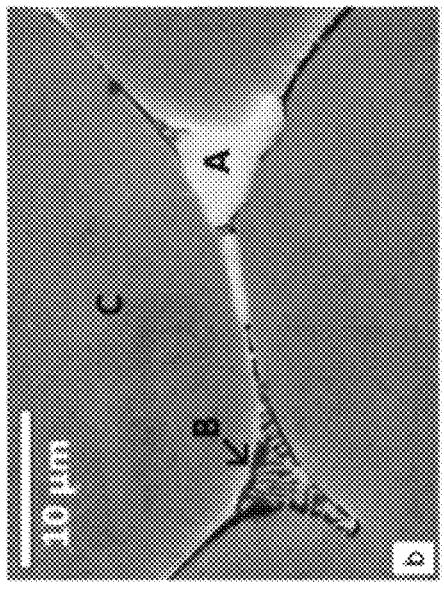
Figure 2C:
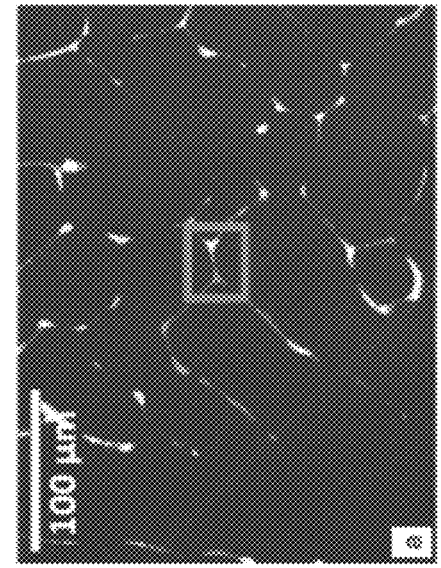
Figure 2D:
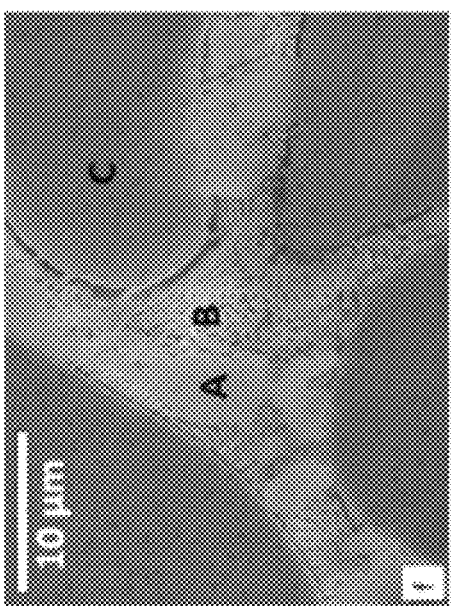
Figure 2E:
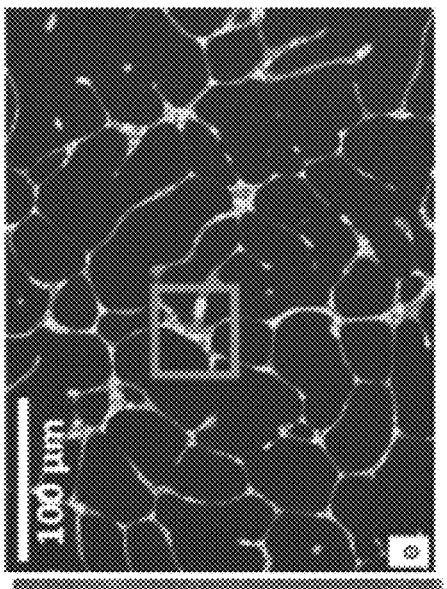
Figure 2F:
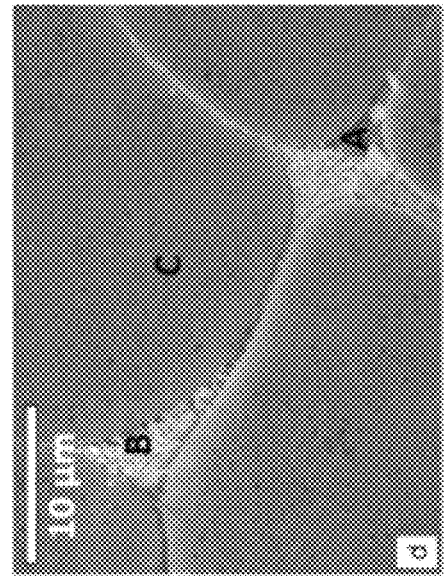

The above examples shows that Mg-0.5Ca-0.5Sr and Mg-1.0Ca-0.5Sr alloys have very similar mechanical properties, but with further increase in Sr and Ca content, the ultimate compression strength decreases. It has been previously reported that the mechanical properties degrade in binary Mg—Ca alloys when Ca content is increased above 1 wt % due to precipitation of Mg2Ca along grain boundaries. Adding 0.5 wt % Sr has a positive effect on the mechanical properties of Mg—Ca as the higher compressive strength is achieved as compared to binary Mg—Ca alloys with similar Ca content. However, addition of 1 wt % Sr reduces the compressive strength as compared to Mg-1.0Ca binary alloy (Wan Y, Xiong G, Luo H, He F, Huang Y, Zhou X. Preparation and characterization of a new biomedical magnesium-calcium alloy. Materials & Design 2008; 29:2034-2037). This can be attributed to the accumulation of greater amounts of eutectic and Sr-rich intermetallics on grain boundaries as seen in FIG. 2E, thereby increasing the brittleness and decreasing the compressive strength at failure. It should also be noted that even though the solubility of Ca in Mg is 0.8 wt % at room temperature, (Chen S L, Daniel S, Zhang F, Chang Y A, Yan X Y, Xie F Y, Schmid-Fetzer R, Oates W A. The PANDAT Software Package and its Applications. CALPHAD 2002; 26:175-188), EDS analysis of cast alloys did not show any Ca or Sr in the Mg matrix except in Mg-1.0Ca-1.0Sr alloy. Therefore, in low Ca and Sr containing cast alloys, the mechanical and electrochemical behavior of the alloys predominantly depends on the secondary phases along grain boundaries.

Upon evaluation of the ICP data detailing the concentration of ions in alloy extracts, it is apparent that the concentrations of $Mg^{2+}$ and $Sr^{2+}$ ions in the alloy extracts from the three alloys with the lowest degradation rate exceed the concentration of $Mg^{2+}$ and $Sr^{2+}$ ions in the as received culture media (note that there are no $Sr^{2+}$ ions present in the as-received culture media). Next, the concentration of $Ca^{2+}$ ions in the alloy extract is lower than in the as-received media. Inductively coupled plasma results coupled with the degradation rate and alloy composition indicate that the concentration of ions in the solution is potentially controlled by two different reaction mechanisms. The first reaction is the dissolution of ions from the alloys into the media due to corrosion while the second reaction is the formation of corrosion products from ions and their deposition on the surface. The increased amount of $Mg^{2+}$ and $Sr^{2+}$ ions as compared to culture media can be directly attributed to the dissolution of the alloys.

Even though Mg-1.0Ca-1.0Sr has the highest degradation rate and has the highest amount of phosphates present on the surface, it also has the highest amount of $Ca^{2+}$ among alloy extracts. This can most likely be attributed to the higher amount of $Ca^{2+}$ going into solution due to fast degradation. On the other hand, Mg-0.5Ca-0.5Sr has the least amount of $Ca^{2+}$ ions present as its Ca content is half of Mg-1.0Ca-1.0Sr, thereby releasing smaller amount of $Ca^{2+}$ ions into the solution. $Sr^{2+}$ ions follow the degradation rate, with Mg-1.0Ca-0.5Sr giving out least amount and Mg-1.0Ca-1.0Sr giving out the maximum amount of $Sr^{2+}$ ions.

The in-vitro cytotoxicity test results show that while the extracts from the Mg-0.5Ca-0.5Sr alloy induced approximately 45% cell death to MC3T3-E1 osteoblasts, the Mg-1.0Ca-0.5Sr alloy showed negligible or very low toxicity for both 50% and 10% extracts at both 3 days and 5 days. Furthermore, when comparing the cytotoxicity of all of the alloy extracts after 5 days to that after 3 days, no significant increase was observed. This demonstrates that there is no rapid increase in cytotoxicity with increase in interaction time with the cells. Interestingly, the cell death for the Mg-0.5Ca-0.5Sr extracts appear to decrease with time. It is unclear at this point if this is related to a decrease in the toxicity of the solution over time as ions may become sequestered, or possibly if released LDH may be unstable once released from lysed cells over the 5 day period.

Conclusions Drawn from Examples 1-9

In this example, Mg-based alloying system with Ca and Sr was investigated for its potential application as degradable orthopedic implant material. The alloys were mainly composed of three phases; α-Mg, $Mg_2Ca$ and $Mg_{17}Sr_2$, which control the mechanical properties and the biocorrosion behavior. The alloys were found to have better mechanical properties than binary Mg—Ca alloys with similar amount of Ca additions. It was found that low amounts of alloying elements enhance the corrosion properties in Hanks' solution, with the optimal composition of Mg-1.0Ca-0.5Sr. At higher concentrations, the degradation rate increases possibly due to formation of higher amount of secondary phases. It was shown that $Mg(OH)_2$ and $(Mg,Ca)_3(PO_4)_2$ precipitated on the surface of the degrading material. Cytotoxicity tests on alloy components demonstrated that Mg-1.0Ca-0.5Sr resulted in almost negligible toxicity, and even the toxicity of Mg-0.5Ca-0.5Sr decreases with time. Collectively, the results conclude that the Mg—Ca—Sr system may be used for biodegradable orthopedic implant applications.

Example 10: Alloy Preparation

It the present example, three binary Mg-x wt % Sr (x=0.5, 1.0, 1.5) alloys and three ternary Mg-x wt % Zn-0.5 wt % Sr (x=2, 4, 6) alloys were prepared using Mg chips (99.98%, Sigma-Aldrich, St. Louis, MO), Sr granules (99.9%, Sigma-Aldrich, St. Louis, MO) and Zn granules (99.99%, Alfa-Aesar, Ward Hill, MA). The elements were mixed in desired proportions and heated at 850° C. in a graphite crucible. The melt was kept at this temperature for 45 minutes and stirred once using graphite rod. The melt was then poured into graphite mould that was kept at room temperature. The entire process of melting and casting was performed in a glove box under argon atmosphere to prevent oxidation.

Example 11: Heat Treatments and Age Hardening Response

Figure 10A:
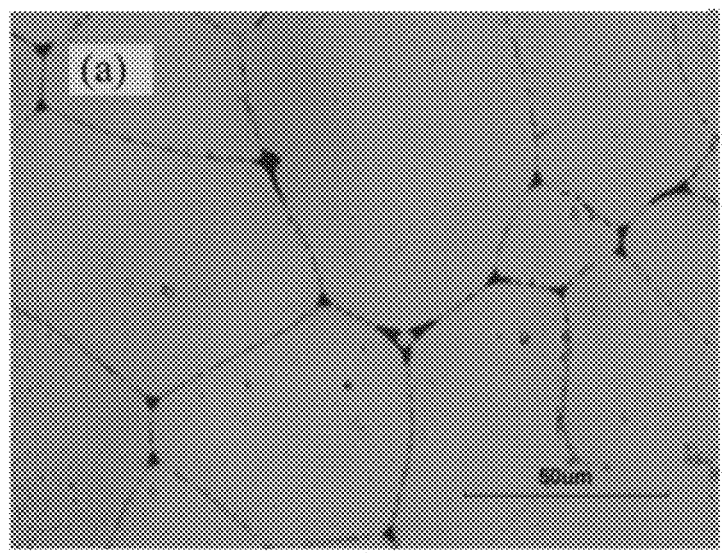
FIGS. 10A-C are optical micrographs of solution treated alloys (FIG. 10A) Mg-0.5Sr (FIG. 10B) Mg-1.0Sr (FIG. 10C) Mg-1.5Sr FIG. 11 demonstrates Vickers microhardness of the binary Mg—Sr alloys.
Figure 10B:
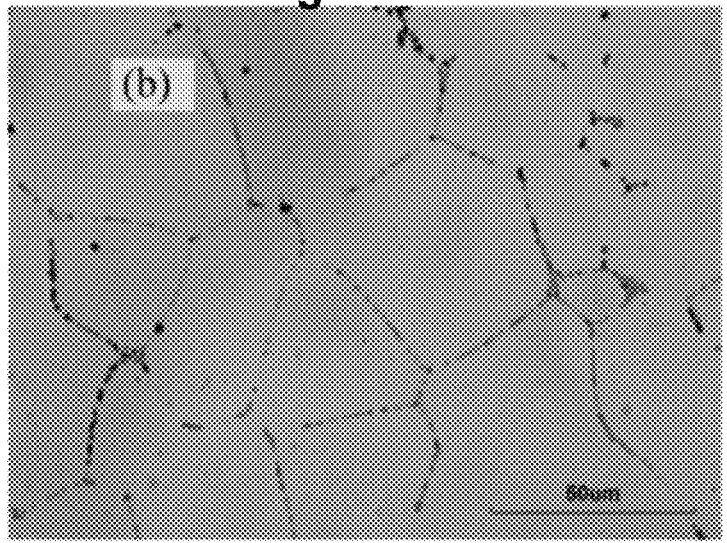
Figure 10C:
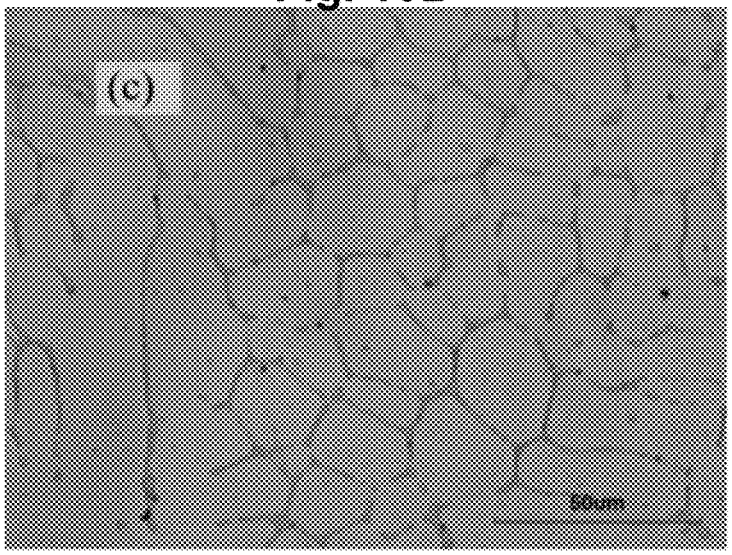

The binary Mg—Sr were encapsulated in quartz tubes under vacuum for homogenization treatments. Mg—Sr alloys were homogenized at 450° C. for 18 hours and quenched in water. The microstructure of binary Mg—Sr alloys is shown in FIGS. 10A-C.

Figure 11:
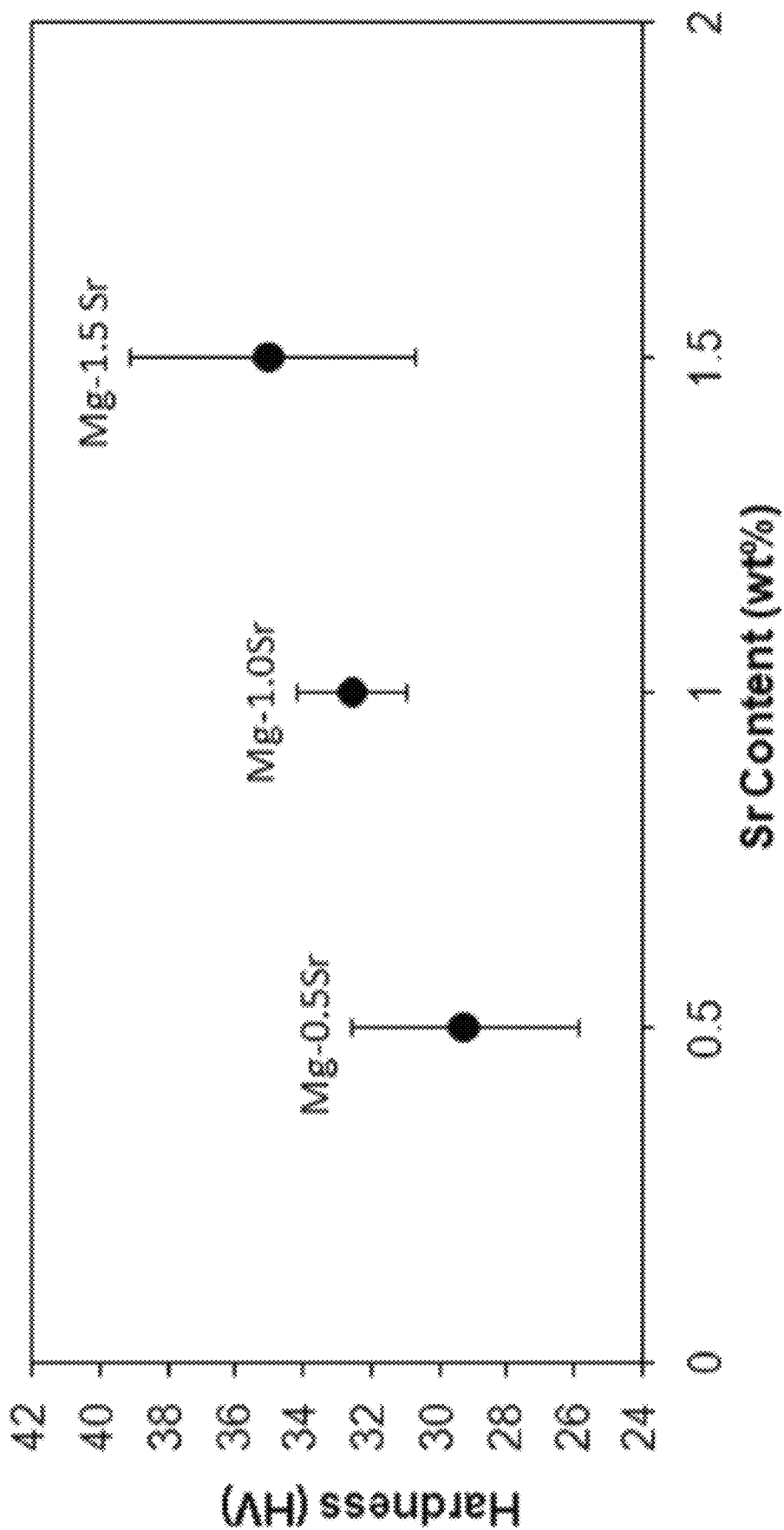

Vicker's microhardness testing was used to measure the hardness of the Mg—Sr alloys. The testing was performed using 300 gf load on the alloys for 15 seconds. All samples were polished to a 0.3 µm finish prior to testing to minimize the influence of surface defects in the analysis. The hardness of the alloys is shown in FIG. 11. It can be seen that the increase in Sr content increases the hardness of the alloys Example 12: Tensile Testing Tensile testing was used to determine the yield strength (YS) and ultimate tensile strength (UTS) of the alloy samples. The alloys were cast into rectangular dog bone shaped samples using a graphite mould. The Mg—Sr tensile samples were homogenized at 450° C. before testing. The mechanical properties of the alloys is shown in Table 5.

TABLE 5

| Mechanical properties of homogenized Mg—Sr. | | |
|---|---|---|
| Alloy | 0.2% YS (MPa) | UTS (MPa) |
| Mg-0.5Sr | 37 | 74 |
| Mg-1.0Sr | 33 | 73 |
| Mg-1.5Sr | 40 | 81 |

Example 13: Dissolution Behavior

Figure 12:
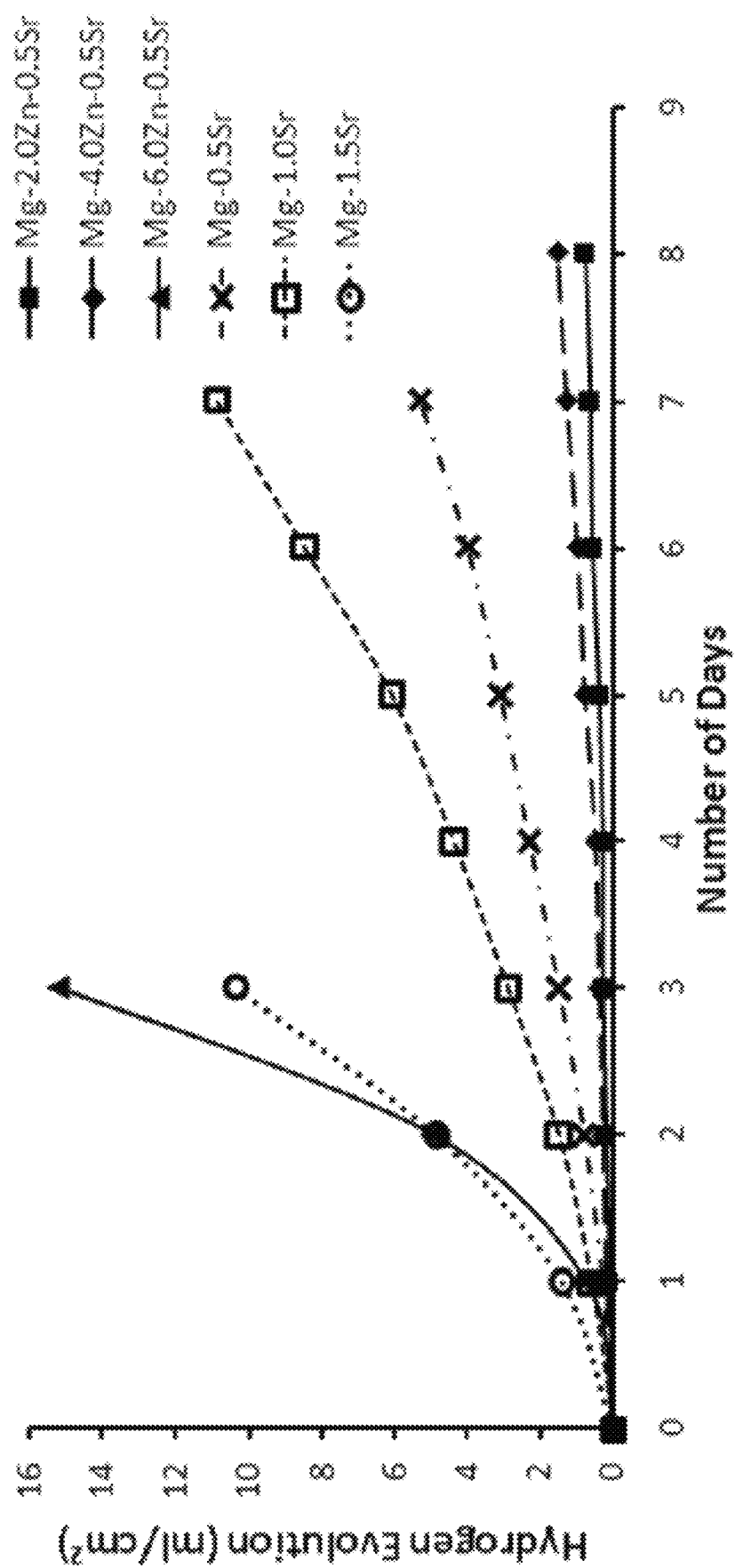
FIG. 12 is a hydrogen evolution plot.

The amount of hydrogen evolution by the binary Mg—Sr and ternary alloys Mg—Zn—Sr in HBSS is shown in FIG. 12. Among Mg—Sr alloys, Mg-0.5Sr alloy had the lowest degradation rate. The degradation rate of the binary increased with increase in Sr content with the best performing alloy being Mg-0.5Sr.

Figure 13B:
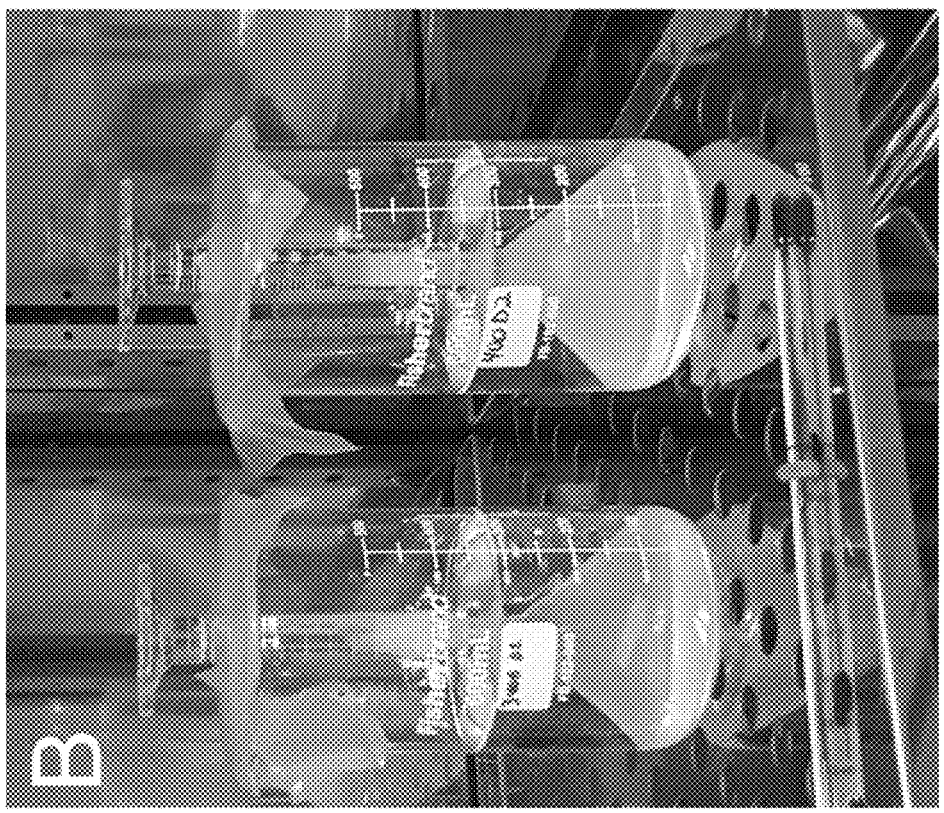
FIG. 13A is a schematic of hydrogen evolution test and FIG. 13B shows two samples undergoing testing.
Figure 13A:
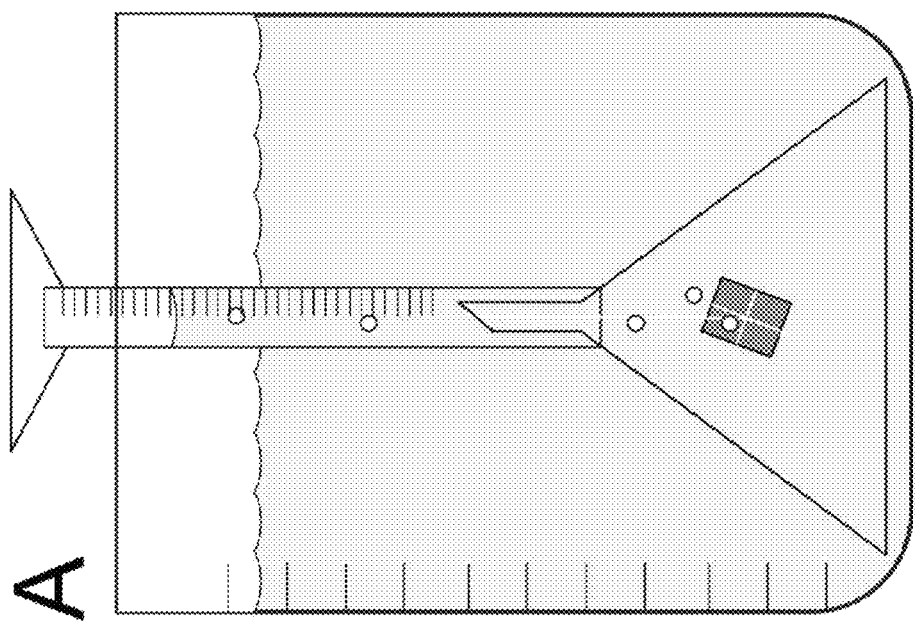
Figure 14:
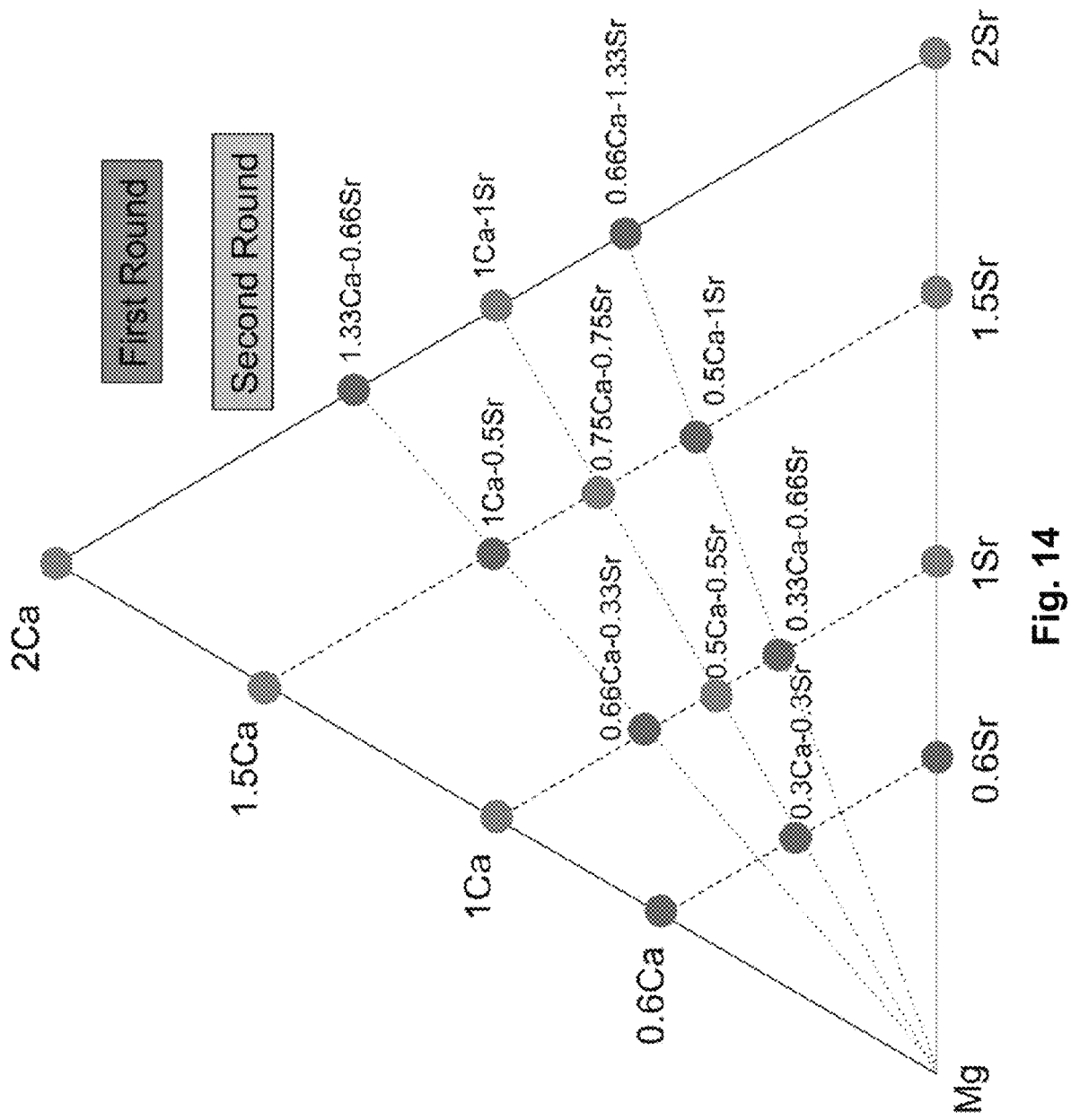
FIG. 14 illustrates experimental points for alloy production, ranging from Mg—Ca to Mg—Sr and in the range of 0.6 wt. % to 2 wt. % alloy addition.

Example 14: Degradation Properties of Alloys in the Mg-Rich Corner of the Mg—Ca—Sr Ternary Phase Diagram Experimental Methods Hydrogen evolution testing is primarily used in this report, as it is facile to determine degradation rate and changes over time. The method is described in other documents, such as the fundamental paper for the patent, Berglund 2012, and is shown schematically in FIGS. 13A-B. $H_2$ is released as a byproduct of Mg dissolution, so by capturing the gas and measuring as a function of time, one can easily determine degradation rate. In vitro degradation rate is a primary screening test of potential Mg-based implant materials. High degradation rates is considered to be unusable, making this a commercially relevant test methodology for the system. A total of eighteen compositions were tested as part of this study, the locations of which are shown in FIG. 14. They include binary Mg—Ca and Mg—Sr alloys in the range of 0.6 to 2 wt. %, along with ternary alloys with Ca:Sr ratios (by weight) of 2:1, 1:1, and 1:2 in the same alloy addition range. Ingots were cast from pure elements into a graphite mold 5×5×2 cm in dimensions. Samples roughly 200 mm$^2$ and around 1 mm thick were sectioned from the same area, 3 per casting. Samples are evaluated in the as-cast condition to remain consistent with previous studies. These 3 samples were suspended in Hank's solution at 37° C. and the H$_2$ evolution rate measured over a time period ranging from 4-12 days, depending on how fast the sample dissolved. During analysis, the H$_2$ volume (in mL) was normalized for sample area and plotted as a function of time. Average degradation rate was determined by fitting a linear model to the data and extracting the slope to give a result in [mL H$_2$/cm$^2$/day].

Microstructure samples were from the same area of castings as the degradation specimens and prepared using standard metallographic mounting and polishing methods. Micrographs were collected on a Leica DM2500 optical microscope in bright field imaging mode. Impurity content was assessed inductively coupled plasma-mass spectrometry (ICP-MS) on an Element2 (Thermo-Finnigan). Computational analysis of the alloy system was performed using Pandat, a thermodynamic simulation software, and database PanMag8.

Results and Discussion

Figure 15:
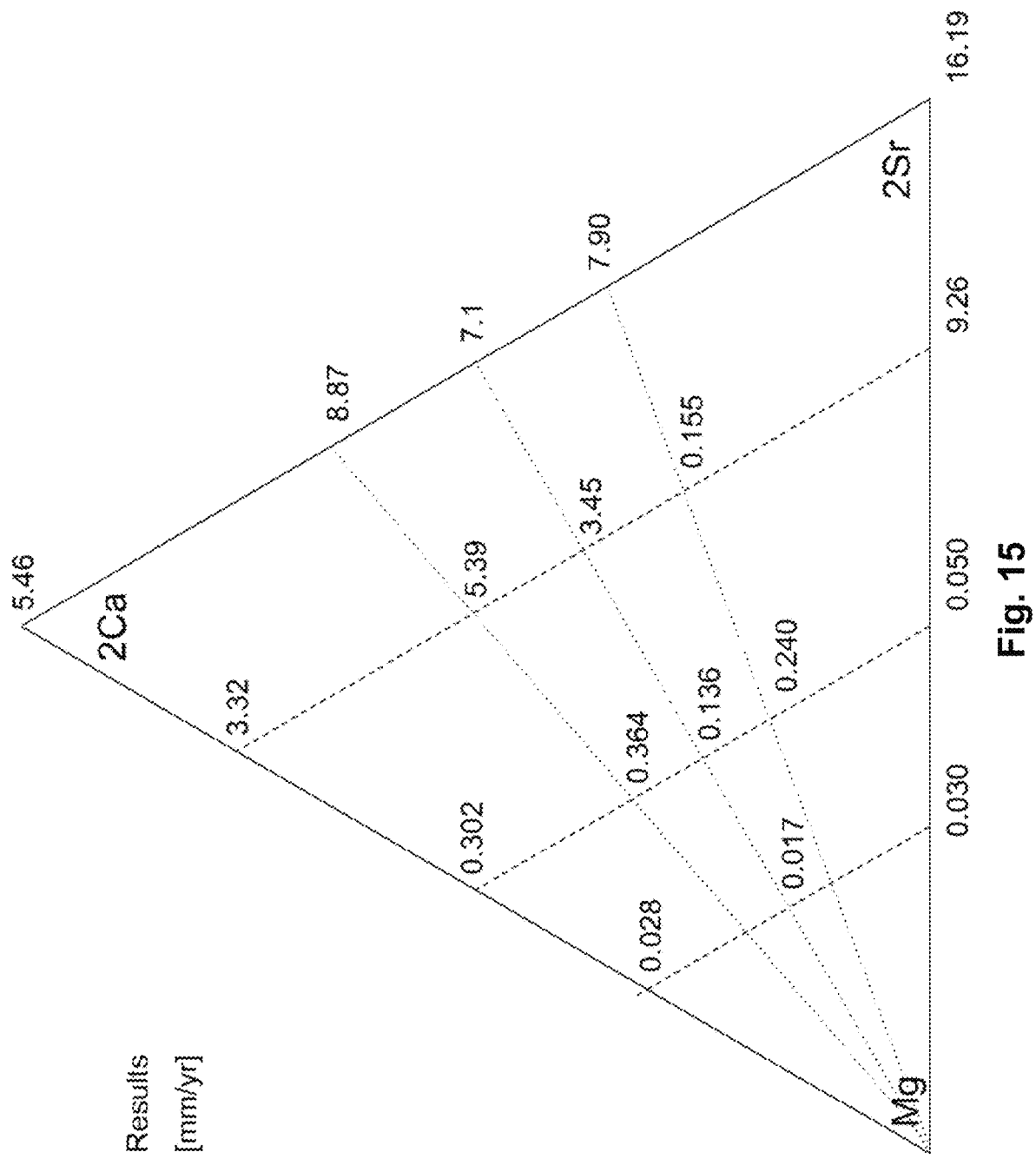
FIG. 15 shows results of degradation testing for compositions listed in FIG. 14. Results are displayed in mm/yr.

The results of degradation testing, converted from mL/cm$^2$/day to mm/yr for display ease (assuming molar equivalence between Mg dissolved and H$_2$ measured), can be seen in FIG. 15. Generally, it was found that higher alloying additions were accompanied by an increase in degradation rate. The degradation rates were very consistent, showing standard deviations of ±10% generally.

Through the use of Pandat, a thermodynamic simulation program, a Sheil solidification reaction as calculated for each alloy. This non-equilibrium condition assumes no diffusion in the solid and infinite diffusion in the liquid, assumptions appropriate for as-cast structures. The results for volume percent particles as a function of alloying addition and precipitate composition are shown in FIG. 16A. Fraction Mg$_{17}$Sr$_2$ is calculated as shown in Equation 1. The results show a gradual increase in total volume fraction of precipitate as composition shifts from Mg—Ca to Mg—Sr binary. Additionally, as expected for alloying elements with very low solubility (like Sr and Ca in Mg), amount of precipitate is roughly proportional to alloying addition. Degradation rates for the alloys are shown in FIG. 16B. Note that Degradation rate is shown in log scale, which deemphasizes the range of degradation rate that spans three orders of magnitude. While it shows that degradation rate is a general function of alloy content, there are significant perturbations in the functions, especially in the 1.5 wt. % sequence of alloys.

$$\frac{vol.\ \%\ Mg_{17}Sr_2}{vol.\ \%\ Mg_{17}Sr_2 + vol.\ \%\ Mg_2Ca} \quad (1)$$

Figure 17:
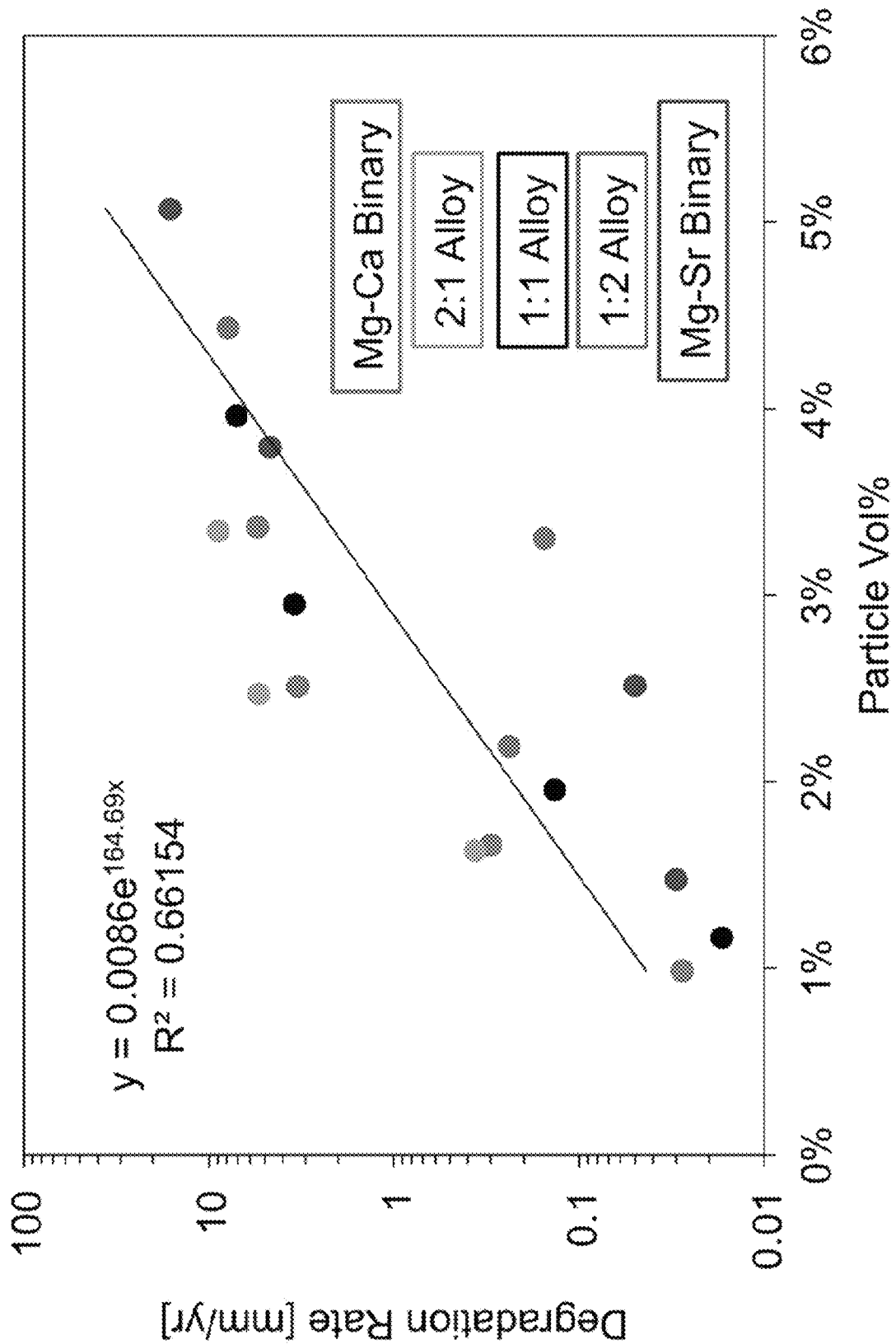
FIG. 17 plots degradation rate as a function of calculated particle volume percent. Colors are correlated to alloying element stoichiometry as indicated in the figure.

Degradation rate of all alloys as a function of calculated volume fraction is presented in FIG. 17, grouped by stoichiometry. Again, the general trend remains that degradation rate correlates with particle volume fraction, but the data is scattered ($R^2$=0.66 for an exponential fit), with some 100× differences in degradation rate at the same volume fraction particles. Curiously, the alloys seem to be grouped into two broad groups of degradation rate: those above 3 mm/year and those below 0.3 mm/year. These groups will be referred to generally as the "fast" and "slow" groups, respectively.

Figure 18:
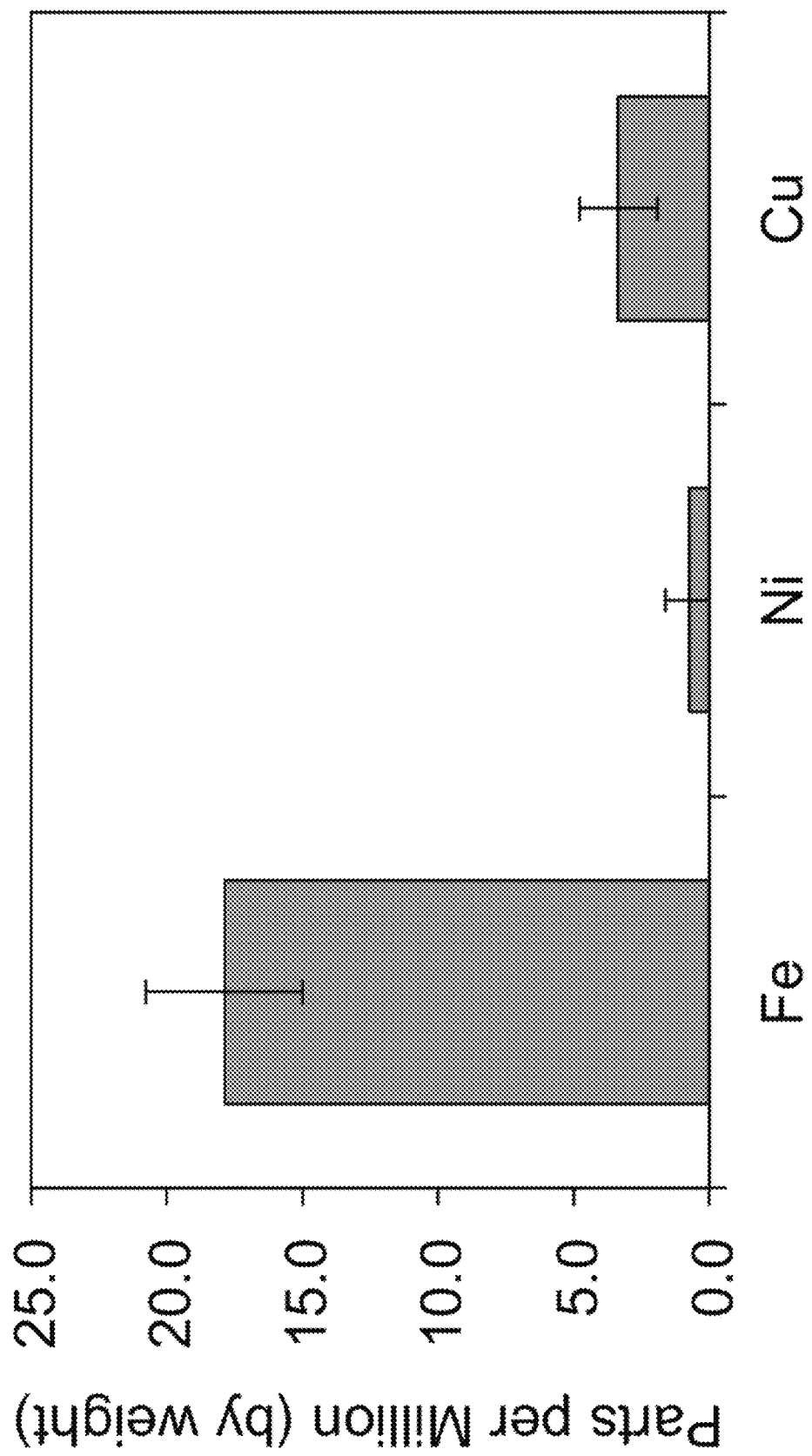
FIG. 18 shows average impurity levels for all samples.

Before further analysis was performed, impurity effects needed to be eliminated. The samples were analyzed by ICP-MS for trace element content of Fe, Ni, and Cu. Because they have extremely low solubility and form no intermetallics with Mg, these elements can form as elemental metal in the microstructure. As they are all significantly higher on the electrochemical series, pockets of these metals in the microstructure act as local cathodes and dramatically increase the corrosion rate. This effect generally occurs above 50 ppm of these trace elements. From the data in FIG. 18, impurity effects are expected to be negligible in these studies.

Subsequently, microstructures were evaluated for indications of degradation rate-determining variables. Upon inspection, one aspect of microstructure stood out as correlating strongly with whether the material degraded in the "fast" or "slow" group: eutectic contiguity, which described how interconnected the eutectic constituent is to itself. A prime example can be seen in FIGS. 19A-B which show the Mg-1Ca-0.5Sr and Mg-0.5Ca-1Sr alloys. These alloys contain identical alloying levels (1.5 total addition) and a similar cellular size, but displayed a 50× difference in degradation rate. Further, of the two, the alloy with the higher volume percent particles (see FIG. 16A) degraded more slowly, contrary to the general trend. Comparing the two microstructures, FIG. 19A (Mg-1Ca-0.5Sr, fast degrading) is much more interconnected, where FIG. 19B (Mg-0.5Ca-1Sr, slow degrading) is globular. Given the relationship between degradation rate and second phase morphology in Mg alloys, this relationship makes sense. The more contiguous the subsurface second phase is, there is more area for electron transfer between the matrix and precipitate, as well as the possibility of grain undermining and release.

Figure 20B:
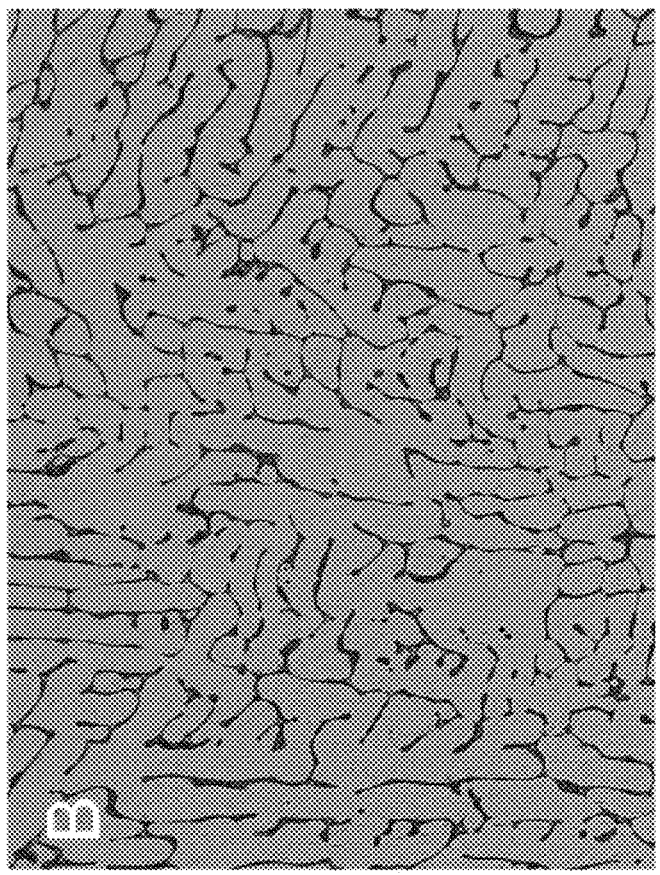
FIGS. 20A-B are examples of triple point analysis for FIG. 20A) Mg-1Ca and FIG. 20B) Mg-2Ca.
Figure 20A:
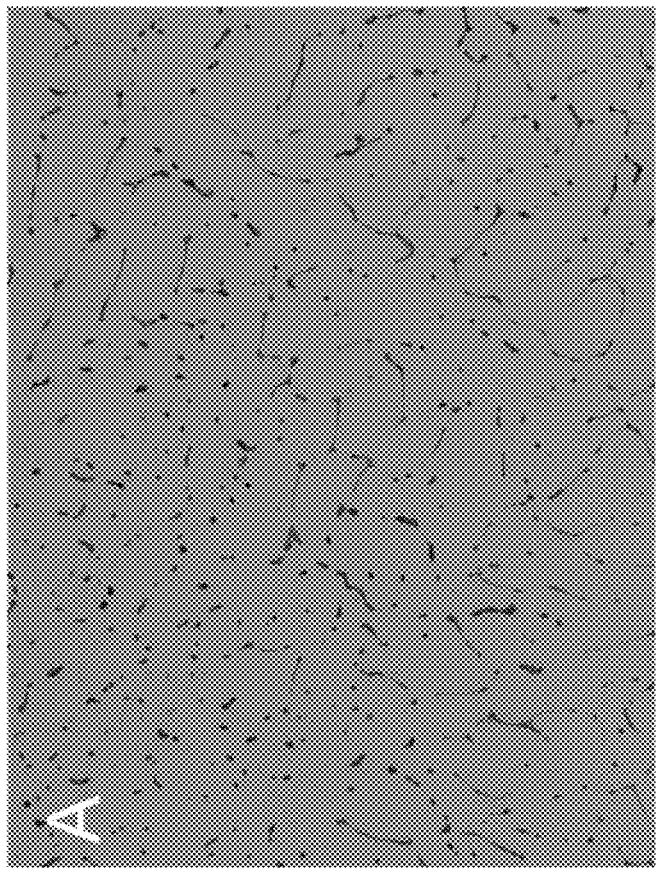

While a qualitative difference in microstructure is relatively facile to determine by visual inspection, quantification is more difficult. In fact, other literature related to second phase contiguity in Mg alloys has stated "no exact quantification of this connectivity is presently available." [Amberger, D 2012] Consequently, a new methodology was developed, by which triple points in the second phase are counted, an extension of triple point junction counting methods of determining grain size. The method counts as a triple point any contiguous second phase region where significant extension in 3 directions is seen. For this study, 3 200× optical micrographs were analyzed per alloy. The micrograph is first inspected and a red dot placed at each triple point junction, as seen in FIGS. 20A-B. Afterward, the dots are counted and averaged. While open to a certain amount of interpretation on what constitutes a triple point junction, this method has the advantage of being insensitive to sample preparation and contrast differences. This is especially important for samples containing the Mg$_{17}$Sr$_2$ precipitate, as it has very low contrast to the Mg matrix in light microscopy, making binary thresholding techniques challenging.

Figures 21A, 21B:
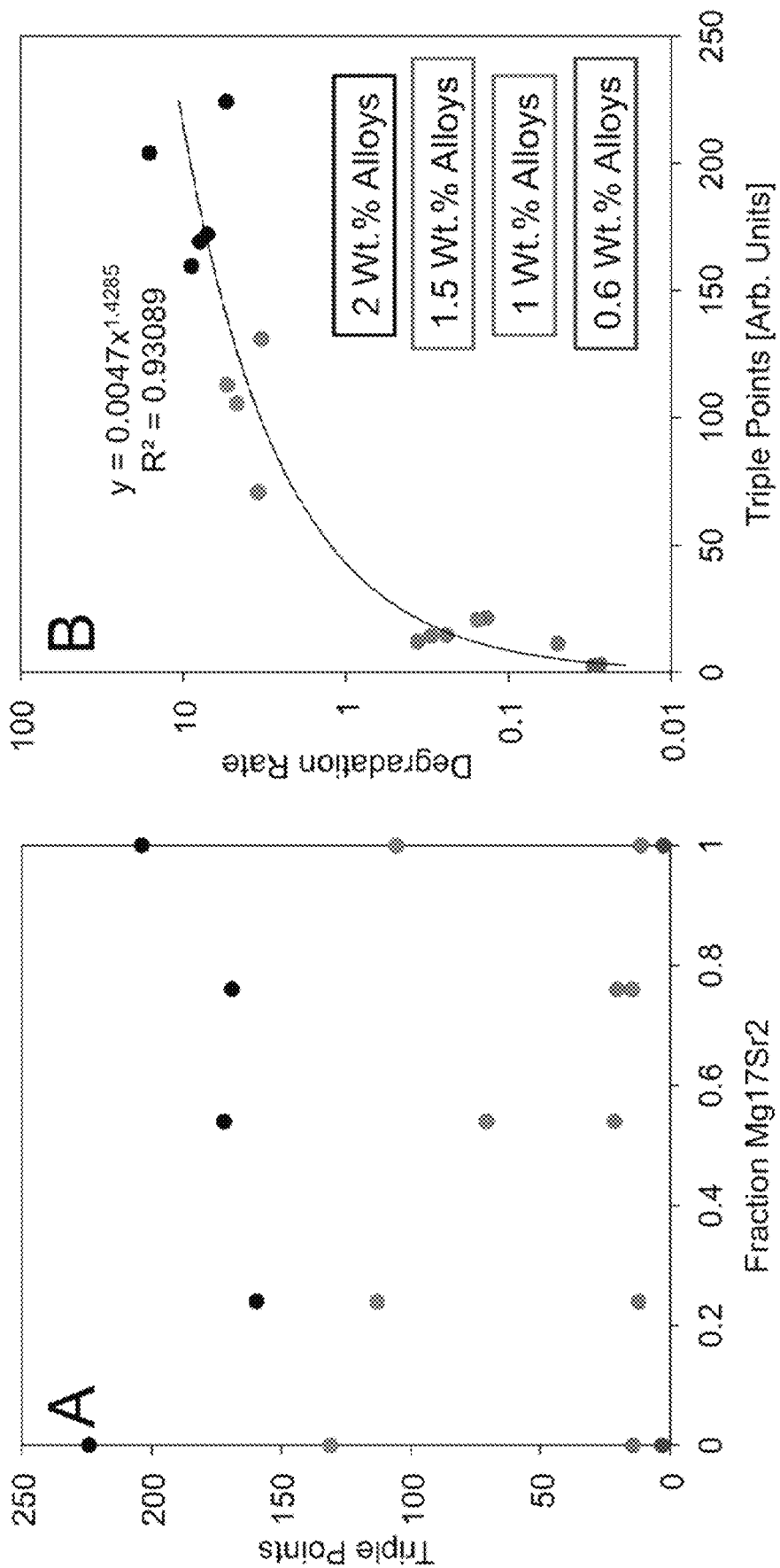
FIG. 21A plots average triple points per image as a function of fraction $Mg_{17}Sr_2$ and wt. % alloying addition (grouped by color).
FIG. 21B plots degradation rate as a function of triple point count, with a power law model fit.

Results of triple point junction counting for all alloys as a function of alloying addition wt. % are shown in FIG. 21A.

Figure 22:
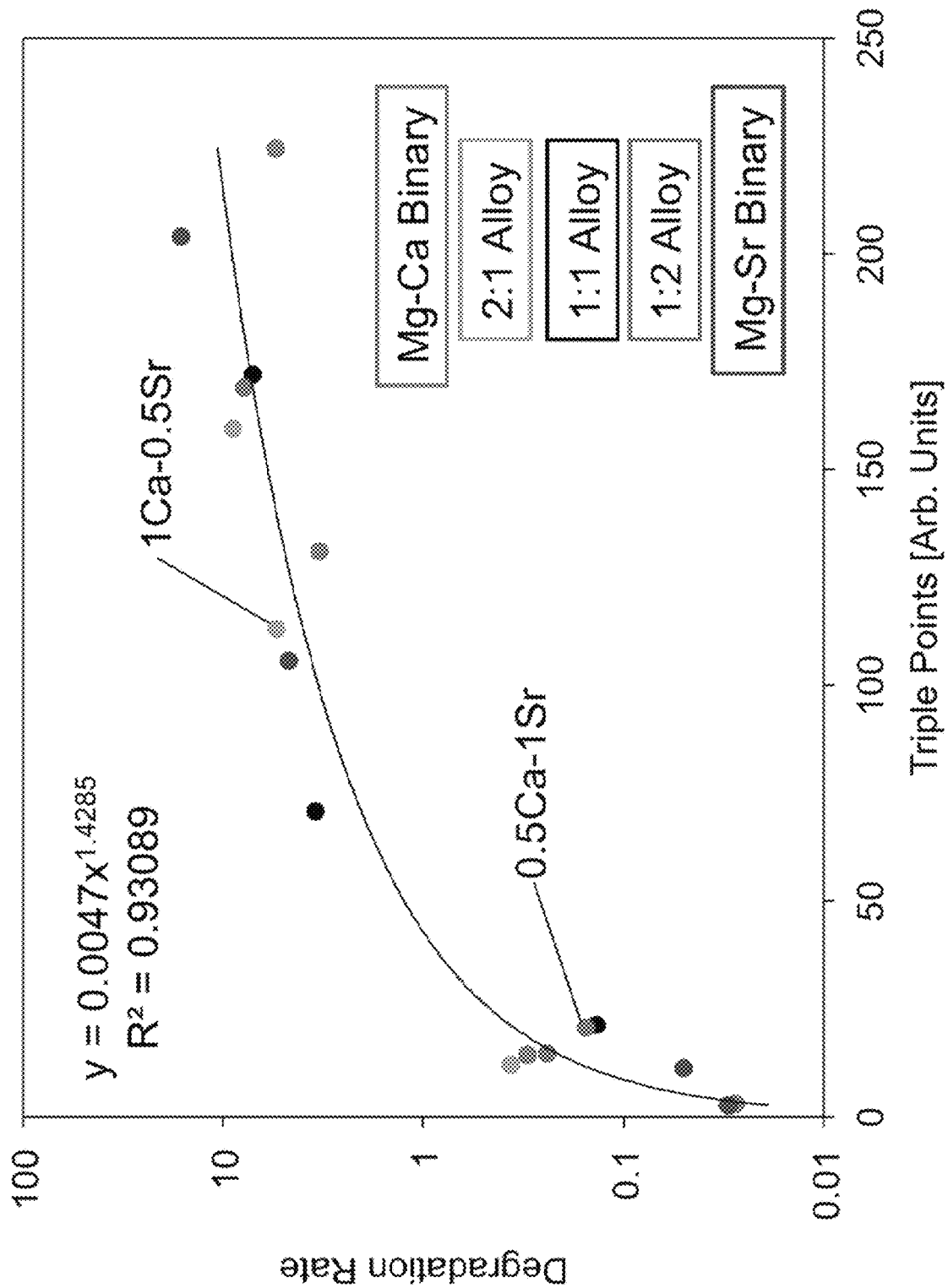
FIG. 22 plots degradation rate vs. triple points, grouped by alloy stoichiometry.

This figure is strikingly similar to FIG. 16B, in which high variability is seen in the 1.5 wt. % addition samples. Contiguity, as measured by triple points, appears to increase with alloying addition, and shows significant range in the 1.5 wt. % series of alloys. The relationship between contiguity and degradation rate is confirmed in FIG. 21B, in which the data falls very well ($R^2$=0.93) on a power law model fit. The data is replotted and grouped by stoichiometry in FIG. 22. Here, it can be seen that the aberrant sample of Mg-0.5Ca-1 Sr falls well in line with the rest of the data. Curiously, in the "fast" group, the Mg—Sr binaries are consistently above the model and the Mg—Ca binaries consistently below. This is likely due to the electrochemical properties of the intermetallics, in which $Mg_2Ca$ is slightly lower on the galvanic series than Mg and $Mg_{17}Sr_2$ slightly higher.

Figure 23:
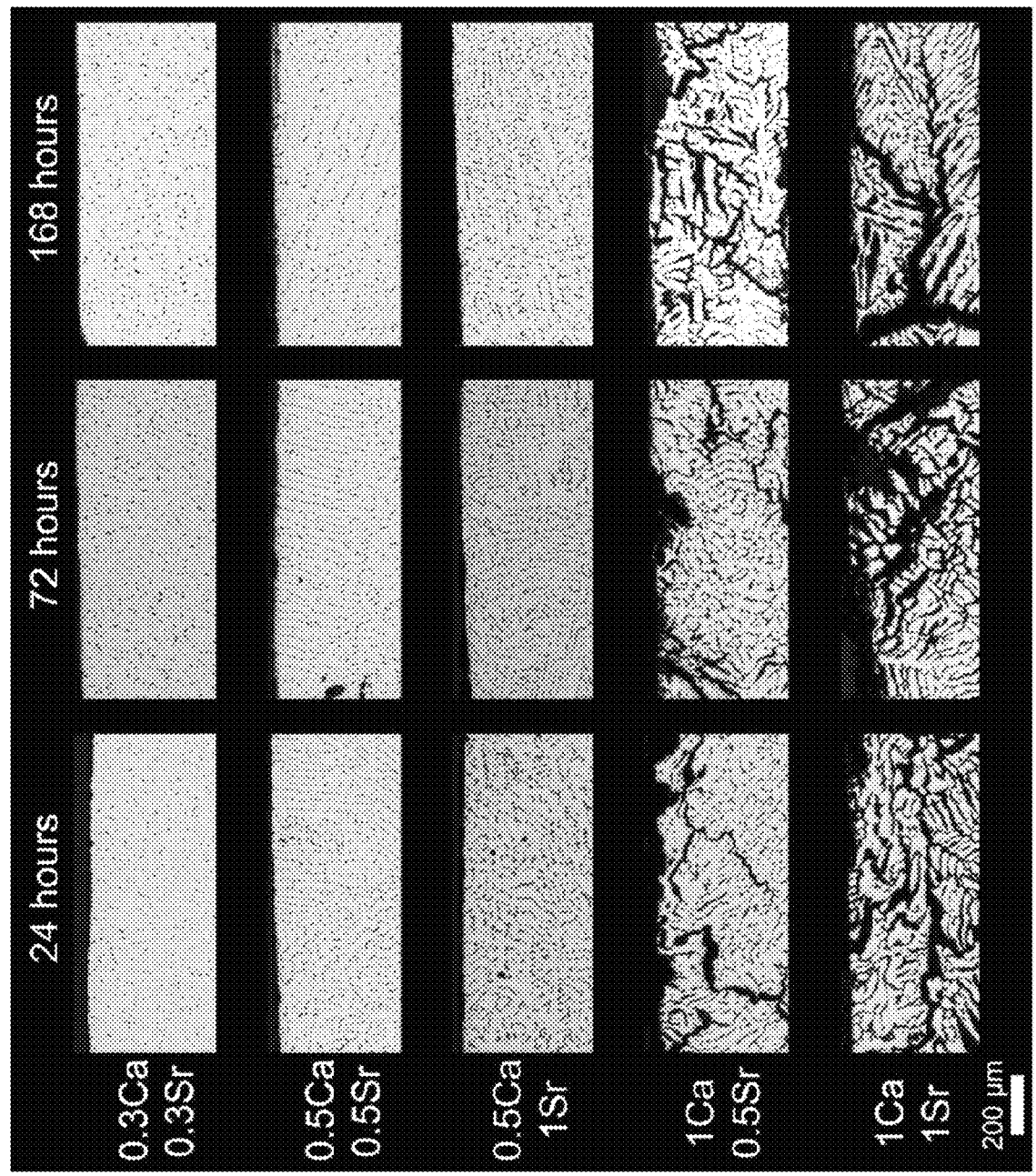
FIG. 23 shows cross-sectional subsurface images of selected samples after immersion for 24, 72, and 168 hours.

Further studies were performed to evaluate the manner in which the microstructure degrades. Samples of selected alloys were tested in Hank's solution and extracted after 24, 72, and 168 hours. They were then encased in quick set acrylic, sectioned across the center, and polished to evaluate the surface topography and subsurface microstructure. The hydrogen evolution measurements were consistent with the previous results, within sample type. The results for all samples are shown in FIG. 23. It can be seen that the samples in the "slow" group experienced mostly uniform degradation, while the two samples in the "fast" group exhibit significant subsurface degradation. More importantly, this subsurface degradation follows the interconnected network of second phase particles, and there is strong evidence for grain undermining accelerating the overall degradation rate.

Figure 19A:
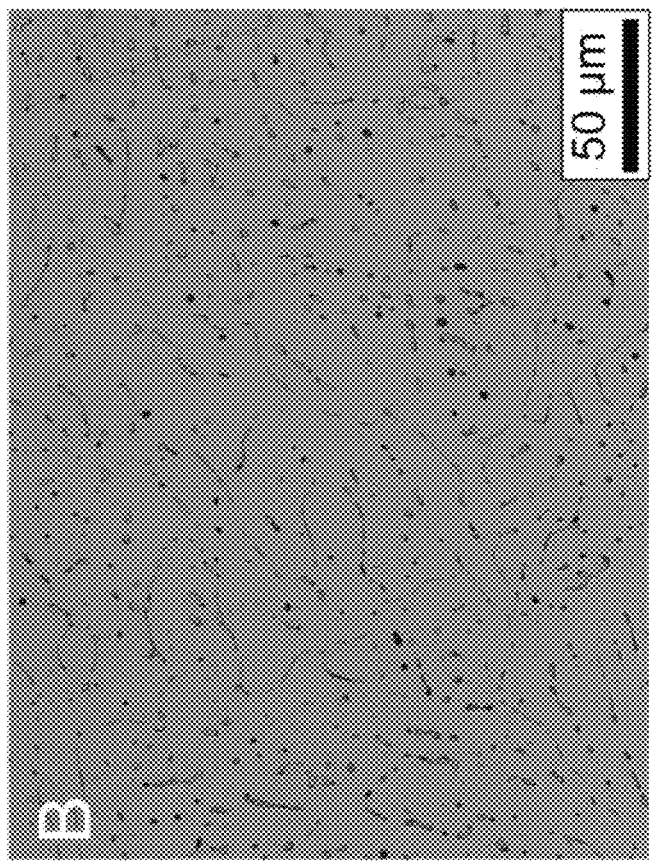
FIGS. 19A-B show microstructure of FIG. 19A) Mg-1Ca-0.5Sr, 5.39 mm/year degradation rate and FIG. 19B) Mg-0.5Ca-1Sr, 0.155 mm/year degradation rate.
Figure 19B:
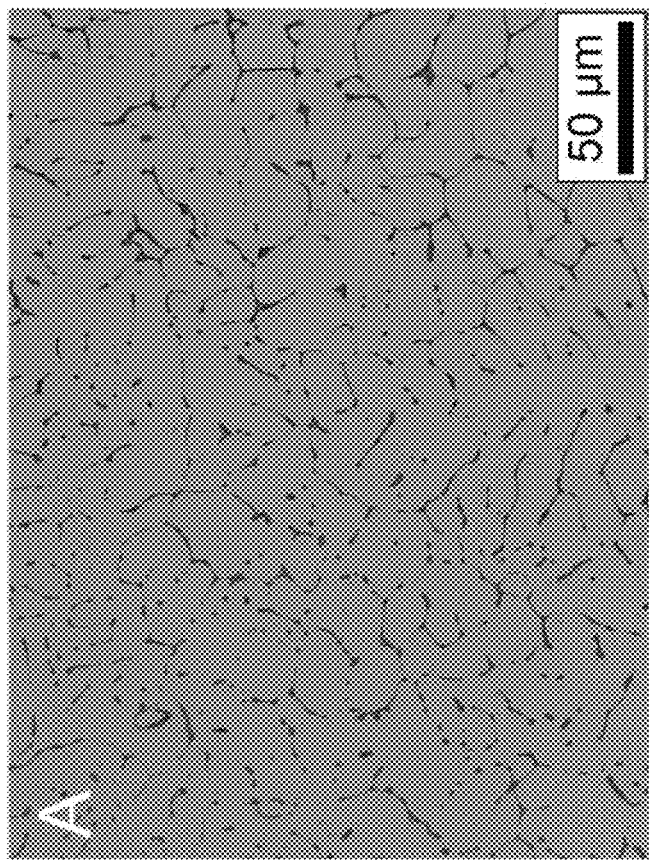

To understand why contiguity changes so drastically as a function of stoichiometry, one must look to the Mg—Ca—Sr phase diagram and follow solidification pathways. Comparing the binary phase diagrams for Mg—Ca and Mg—Sr, it is seen that while the alloys have similar construction, the eutectic temperature for Mg—Sr is much higher than for Mg—Ca. The consequence of this to the ternary diagram can be seen in the pseudobinaries in FIG. 24. This figure follows the three dotted lines projecting from the 100% Mg corner of the ternary phase diagram in FIG. 15. When mixed, the (Liquid+α+$Mg_{17}Sr_2$) phase field dominates well into the Ca-rich side of the diagram. Consequently, for a 0.5Ca-1Sr alloy (along 0.5Ca in FIG. 25C), as solidification progresses, the alloy forms primary a dendrites, then a significant amount of $Mg_{17}Sr_2$ in the liquid interstices by nucleation and growth, before a eutectic reaction freezes the remaining liquid. This results in globular $Mg_{17}Sr_2$ particles dominating the "eutectic" structure (FIG. 19B). Conversely, for a 1Ca-0.5Sr alloy (along 1Ca in FIG. 25A), very little $Mg_{17}Sr_2$ is formed prior to the eutectic reaction, resulting in a more typical eutectic morphology (FIG. 19A).

Looking back at FIG. 16B, which summarized the degradation rate data, it is evident that there are significant deviations from linear between results for the binary alloys. For the 2% addition line, rate jumps as one moves from Mg—Ca to Mg—Sr, then decreases, then end at the highest point for the Mg—Sr binary alloy. It appears that at higher concentrations (1.5-2 wt. %), Mg—Sr dissolves at a faster rate than Mg—Ca. This could be explained by either the higher volume fraction of particles (FIG. 16A) or by the electrochemical potential of the second phases. Between these two extremes, it was found that eutectic contiguity decreases systematically (FIG. 21A) for the 2% and 1.5 wt. % alloys. Overall, the data indicate that more Ca and Sr are able to be included in the material than the binaries without negative consequences on degradation rate for the ternary alloys than for the binaries alone.

CONCLUSIONS

A survey of 18 Mg—Ca—Sr ternary, along with Mg—Ca and Mg—Sr binary, alloys has demonstrated that there are significant non-linear effects on degradation upon mixing alloying elements. These effects are shown to be most accurately predictable by eutectic contiguity, as measured by eutectic microconsituent triple point density. This mechanism was confirmed with subsurface imaging techniques. Solidification microstructure in these alloys is a direct consequence of the ratio of alloying elements, but not predictable based only on the binaries.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

The invention claimed is:

1. A structure comprising an alloy having:
calcium and strontium, wherein the sum of calcium and strontium is from 0.6 to 1.5 weight percent;
an impurity in the amount of less than 50 ppm; and
the balance of the alloy is magnesium.

2. The structure of claim 1, wherein calcium is at least 0.3 weight percent of the alloy, and strontium is at least 0.3 weight percent of the alloy.

3. The structure of claim 1, wherein impurity is iron, nickel, or copper.

4. The structure of claim 1, wherein the alloy is a bioresorbable, non-toxic, osteogenic magnesium alloy.

5. The structure of claim 1, wherein the structure is a non-toxic, non-immunoreactive orthopedic implant.

6. The structure of claim 1, wherein the alloy comprises at least 50 percent total weight of the structure.

7. The structure of claim 1, wherein the structure is a spinal implant.

8. The structure of claim 7, wherein the spinal implant is a cage, dowel or wedge.

9. The structure of claim 7, wherein the spinal implant is a rod, screw, pin or plate.

10. The structure of claim 1, wherein the structure is a dental implant.

11. The structure of claim 1, wherein the structure is selected from the group consisting of: cannulated screw for femoral head fixation, fracture fixation screw and plate system, suture anchor, interference screw, surgical clip, and vascular stent.

12. The structure of claim 1, wherein the structure is a prosthetic femoral hip joint; a prosthetic femoral head; a prosthetic acetabular cup; a prosthetic elbow; a prosthetic knee; a prosthetic shoulder; a prosthetic wrist; a prosthetic ankle; a prosthetic hand; a prosthetic finger; a prosthetic toe; a prosthetic vertebrae; a prosthetic spinal disc; a prosthetic cochlea; a prosthetic vessel; or a prosthetic heart valve.

\* \* \* \* \*